(12) United States Patent
    Thapliyal

(10) Patent No.: US 10,292,815 B2
(45) Date of Patent: May 21, 2019

(54) PERSONALIZED AORTIC VALVE PROSTHESIS

(71) Applicant: AneuMed, Inc., Los Altos, CA (US)

(72) Inventor: Hira V. Thapliyal, Los Altos, CA (US)

(73) Assignee: AneuMed, Inc., Los Altos, CA (US)

( * ) Notice: Subject to any disclaimer, the term of this patent is extended or adjusted under 35 U.S.C. 154(b) by 0 days.

(21) Appl. No.: 15/638,277

(22) Filed: Jun. 29, 2017

(65) Prior Publication Data

US 2017/0296335 A1    Oct. 19, 2017

Related U.S. Application Data

(62) Division of application No. 14/267,453, filed on May 1, 2014, now Pat. No. 9,717,592.

(Continued)

(51) Int. Cl.
   *A61F 2/24*    (2006.01)
   *A61F 2/06*    (2013.01)
   (Continued)

(52) U.S. Cl.
   CPC .......... *A61F 2/2415* (2013.01); *A61F 2/2418* (2013.01); *D04C 1/08* (2013.01);
   (Continued)

(58) Field of Classification Search
   CPC ...... A61F 2/2415; A61F 2/856; A61F 2/2412; A61F 2/2418; A61F 2/30942; A61F 2002/508; A61F 2002/061
   See application file for complete search history.

(56) References Cited

U.S. PATENT DOCUMENTS

| 5,741,215 A | 4/1998 | D'Urso |
| 6,849,088 B2 | 2/2005 | Dehdashtian et al. |

(Continued)

FOREIGN PATENT DOCUMENTS

| CN | 1985775 A | 6/2007 |
| CN | 101961269 A | 2/2011 |

(Continued)

OTHER PUBLICATIONS

English Translation of FR 2 858 208 A1 (inlcuded in applicant's IDS dated Apr. 26, 2018).*

(Continued)

*Primary Examiner* — Brian A Dukert
(74) *Attorney, Agent, or Firm* — Schwegman Lundberg & Woessner, P.A.

(57) ABSTRACT

A personalized prosthetic valve for implantation at a native valve treatment site includes a self-expanding mesh and a plurality of valve leaflets coupled to the mesh. The mesh may be delivered to the native valve in a collapsed configuration, and in an expanded configuration the mesh engages the native valve. The mesh in the expanded configuration is also personalized to match the treatment site, such that the outer mesh surface substantially matches the treatment site shape and size. The self-expanding mesh forms a central lumen configured to allow blood or other body fluids to pass therethrough. In the open configuration, blood passes through the prosthetic valve, and in the closed configuration, the plurality of leaflets are closer together and blood is prevented from flowing upstream through the prosthetic valve.

14 Claims, 23 Drawing Sheets

Related U.S. Application Data

(60) Provisional application No. 61/817,993, filed on May 1, 2013.

(51) Int. Cl.
  *D04C 1/08* (2006.01)
  *A61F 2/856* (2013.01)

(52) U.S. Cl.
  CPC ......... *A61F 2/856* (2013.01); *A61F 2002/061* (2013.01); *A61F 2240/002* (2013.01); *A61F 2240/004* (2013.01); *D10B 2509/06* (2013.01)

(56) References Cited

U.S. PATENT DOCUMENTS

| | | | |
|---|---|---|---|
| 7,371,067 | B2 | 5/2008 | Anderson et al. |
| 7,771,467 | B2 | 8/2010 | Svensson |
| 8,057,396 | B2 | 11/2011 | Forster et al. |
| 9,717,592 | B2 | 8/2017 | Thapliyal |
| 2007/0150052 | A1 | 6/2007 | Santilli |
| 2007/0293936 | A1 | 12/2007 | Dobak, III |
| 2008/0275548 | A1 | 11/2008 | Svensson |
| 2010/0234937 | A1 | 9/2010 | Wang et al. |
| 2010/0286768 | A1 | 11/2010 | Alkhatib |
| 2011/0319989 | A1 | 12/2011 | Lane et al. |
| 2012/0101567 | A1 | 4/2012 | Jansen |
| 2013/0296998 | A1* | 11/2013 | Leotta .................. G05B 15/02 623/1.11 |
| 2014/0088698 | A1 | 3/2014 | Roels et al. |
| 2014/0330367 | A1 | 11/2014 | Thapliyal |

FOREIGN PATENT DOCUMENTS

| | | |
|---|---|---|
| EP | 1849440 A1 | 10/2007 |
| EP | 2710978 A1 | 3/2014 |
| EP | 2991587 A2 | 3/2016 |
| FR | 2858208 A1 | 2/2005 |
| JP | 2016520382 A | 7/2016 |
| WO | WO-2013028387 A2 | 2/2013 |
| WO | WO-2013036168 A1 | 3/2013 |
| WO | WO-2013037519 A1 | 3/2013 |
| WO | WO-2014026870 A2 | 2/2014 |
| WO | WO-2014179618 A2 | 11/2014 |

OTHER PUBLICATIONS

De Prado, et al. Time course of reendothelialization of stents in a normal coronary swine model: characterization and quantification. Vet Pathol. Nov. 2011;48(6):1109-17. doi: 10.1177/0300985811400446. Epub Mar. 10, 2011.

European search report and search opinion dated Apr. 20, 2016 for EP Application No. 14791076.4.

International search report and written opinion dated Dec. 24, 2014 for PCT Application No. US2014/036450.

Notice of allowance dated Jun. 7, 2017 for U.S. Appl. No. 14/267,453.

Office action dated Sep. 19, 2016 for U.S. Appl. No. 14/267,453.

Office action dated Dec. 30, 2015 for U.S. Appl. No. 14/267,453.

"European Application Serial No. 14791076.4, Communication Pursuant to Article 94(3) EPC mailed Oct. 12, 2017", 5 pgs.

"European Application Serial No. 14791076.4, Response filed Apr. 19, 2018 to Communication Pursuant to Article 94(3) EPC mailed Oct. 12, 2017", 10 pgs.

"European Application Serial No. 14791076.4, Response filed Nov. 21, 2016 to Extended European Search Report dated Apr. 20, 2016", 50 pgs.

"International Application Serial No. PCT/US2014/036450, International Preliminary Report on Patentability dated Nov. 12, 2015", 10 pgs.

"International Application Serial No. PCT/US2014/036450, Invitation to Pay Additional Fees and Partial Search Report dated Sep. 22, 2014", 2 pgs.

"U.S. Appl. No. 14/267,453, Applicant's Summary of Examiner Interview filed Apr. 11, 2017", 1 pg.

"U.S. Appl. No. 14/267,453, Examiner Interview Summary dated Apr. 4, 2017", 3 pgs.

"U.S. Appl. No. 14/267,453, Examiner Interview Summary dated Jun. 13, 2016", 3 pgs.

"U.S. Appl. No. 14/267,453, Response filed Mar. 17, 2017 to Final Office Action dated Sep. 19, 2016", 7 pgs.

"U.S. Appl. No. 14/267,453, Response filed Apr. 29, 2016 to Non Final Office Action dated Dec. 30, 2015", 7 pgs.

"U.S. Appl. No. 14/267,453, Response filed Dec. 15, 2015 to Restriction Requirement dated Oct. 15, 2015", 1 pg.

"U.S. Appl. No. 14/267,453, Restriction Requirement dated Oct. 15, 2015", 9 pgs.

"U.S. Appl. No. 14/267,453, Supplemental Amendment filed Jun. 8, 2016", 8 pgs.

"Japanese Application Serial No. 2016-512050, Office Action dated Mar. 13, 2018", w/ English Translation, 9 pgs.

"Japanese Application Serial No. 2016-512050, Response filed Sep. 11, 2018 to Office Action dated Mar. 13, 2018", w/ English Claims, 9 pgs.

"Japanese Application Serial No. 2016-512050, Examiners Decision of Final Refusal dated Feb. 15, 2019", W/ English Translation, 5 pgs.

\* cited by examiner

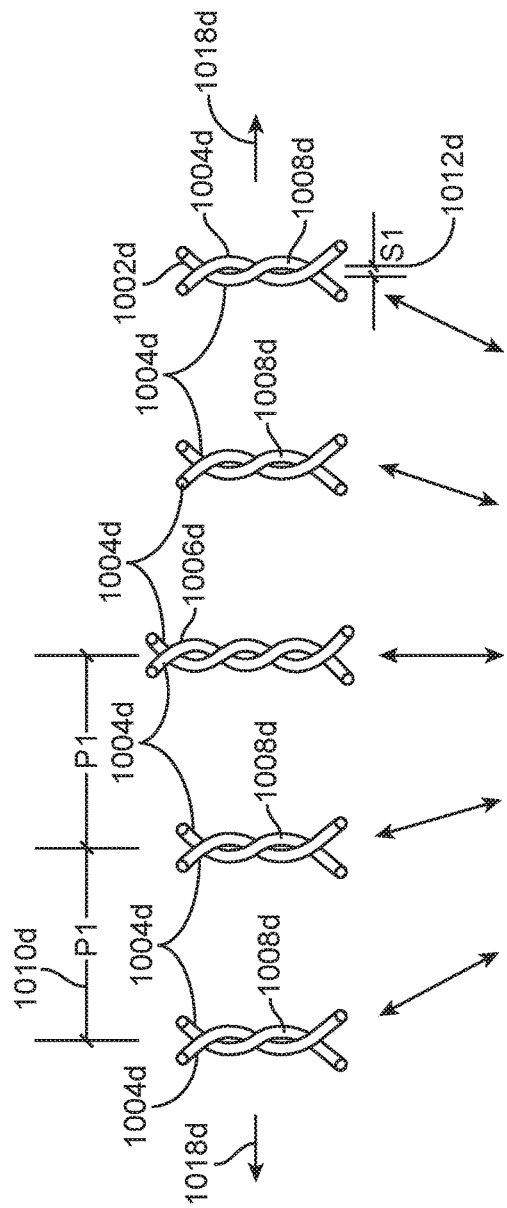
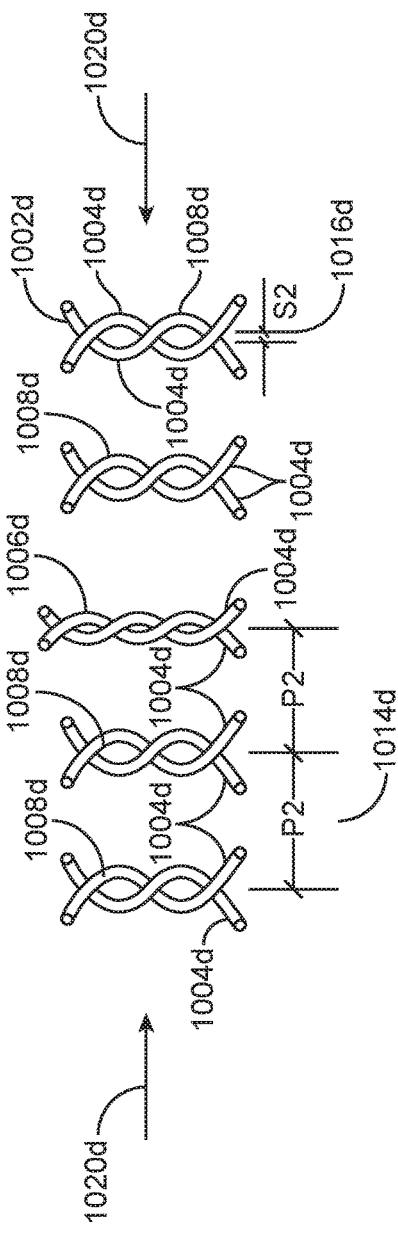
FIG. 12E
FIG. 12F

PERSONALIZED AORTIC VALVE PROSTHESIS

CROSS-REFERENCE TO RELATED APPLICATIONS

The present application is a divisional of U.S. patent application Ser. No. 14/267,453 now U.S. Pat. No. 9,717,592 filed on May 1, 2014 which is a non-provisional of, and claims the benefit of U.S. Provisional Patent Application No. 61/817,993 filed May 1, 2013; the entire contents of which are incorporated herein by reference.

The present application is related to U.S. patent application Ser. No. 13/663,160 (WSGR ref 44600-703.201 formerly 22520-703.201) filed Oct. 29, 2012; the entire contents of which are incorporated herein by reference.

BACKGROUND OF THE INVENTION

Field of the Invention

The present application generally relates to medical devices and methods. More particularly, the present invention relates to the fabrication and use of personalized medical prostheses that conform in size and/or shape to the anatomy of their intended locations in human body. More specifically, the present application relates to the structure of the self expanding, anatomically conformal prosthesis as a replacement for the aortic valve of the human body.

Native valves in the human body can fail for a number of reasons. Traditional surgical methods have been used to repair these valves but this often requires major surgery and a lengthy recovery period. Newer minimally invasive techniques are promising, but it can be difficult to accurately deliver a prosthetic valve and anchoring the prosthesis may also be challenging. Furthermore, prosthetic valves also can develop perivalvular leaks. Therefore, it would be desirable to provide improved prosthetic valves that can be easily delivered, securely anchored, and that do not leak. At least some of these objectives will be satisfied by the exemplary embodiments disclosed below.

The terms 'mesh' and "frame" are used interchangeably in this application to denote the prostheses which are being deployed in the aortic valve location in the aorta. Exemplary embodiments are directed at aortic valves, but this is not intended to be limiting and one of skill in the art will appreciate that any number of valves may be treated using the prostheses disclosed herein, including but not limited to other heart valves, venous valves, or other anatomical valve structures.

SUMMARY OF THE INVENTION

The present application generally relates to the structure of the self expanding frame as a replacement for native valves such as the aortic valve in the body. More specifically, the invention describes a structure of a conformal frame constructed for a specific aortic sinus anatomy. The frame has anatomically accurate placement of the ostia for the coronary arteries in the aortic sinus which allows for access to the coronary arteries for coronary interventions after implantation of the prosthetic valve, if needed. In addition, the frame has a membrane disposed on a portion thereof to protect against perivalvular leaks.

A main aspect of the present disclosure is to describe a structure and a method the fabrication of a mesh which matches the anatomy of a given patient. The details of this are given in the full description of the accompanying drawings.

In a first aspect of the present invention, a method for manufacturing a personalized prosthetic valve comprises providing one or more images of a native valve, creating a digital data set characterizing shape and size of the native valve based on the one or more images, and transforming the digital data set into machining instructions. The method also comprises forming a mandrel using the machining instructions, wherein the mandrel has a shape that substantially matches the treatment site shape, applying a mesh to the mandrel, and heat treating the mesh while the mesh is disposed on the mandrel so that the mesh is biased to return to a shape matching the shape of the treatment site thereby forming the personalized prosthetic valve. The personalized prosthetic valve has a contracted configuration and an expanded configuration. In the contracted configuration, the prosthetic valve is adapted to be delivered to the native valve, and the prosthetic valve is biased to return to the expanded configuration which substantially matches the shape of the native valve.

In another aspect of the present invention, a personalized prosthetic valve for implantation at a native valve treatment site comprises a self-expanding mesh having a collapsed configuration and an expanded configuration. The collapsed configuration is adapted to be delivered to the native valve treatment site, and the expanded configuration is adapted to expand the personalized prosthetic valve into engagement with the treatment site. The mesh in the expanded configuration is personalized to match the treatment site, and the mesh has an outer surface that substantially matches the treatment site shape and size in the expanded configuration. The self-expanding mesh forms a central lumen that is configured to allow blood or other body fluids to pass therethrough. The personalized prosthetic valve further comprises a plurality of valve leaflets coupled to the self-expanding mesh and has an open configuration and a closed configuration. In the open configuration blood is free to pass through the prosthetic valve, and in the closed configuration the plurality of leaflets are closer toward one another than in the open configuration, and blood is prevented from flowing upstream through the prosthetic valve.

In another aspect of the present invention a personalized prosthetic valve for implantation at a native valve treatment site comprises a self-expanding mesh having a collapsed configuration and an expanded configuration. The collapsed configuration is adapted to be delivered to the native valve treatment site, and the expanded configuration is adapted to expand the valve into engagement with the treatment site. The mesh in the expanded configuration is personalized to match the treatment site, and the mesh has an outer surface that substantially matches the native valve treatment site shape and size in the expanded configuration. The self-expanding mesh forms a central lumen configured to allow blood or other body fluids to pass therethrough, and the valve further comprises a plurality of valve leaflets coupled to the self-expanding mesh and that have an open configuration and a closed configuration. In the open configuration the blood or the other body fluids are free to pass through the valve, and in the closed configuration the plurality of leaflets are closer toward one another than in the open configuration, and the blood or the other body fluids are prevented from flowing upstream through the prosthetic valve.

The self-expanding mesh may comprise nitinol, or the mesh may comprise one or more filaments in a helical pattern. The self-expanding mesh may comprise one or more filaments woven together to form overlapping regions with the one or more filaments overlapping one another at least once. The one or more filaments may be woven together to form a first overlapping region and a second overlapping region. The first overlapping region the filaments may overlap with one another a first number of times, and in the second overlapping region the filaments may overlap with one another a second number of times different than the first number of times. The self-expanding mesh may comprise barbs or hooks adapted to engage tissue at the treatment site and anchor the personalized prosthesis. The plurality of overlapping filaments may form overlapping regions, and the overlapping regions may form raised surfaces adapted to engage tissue at the native valve treatment site and anchor the personalized prosthetic valve.

The personalized prosthetic valve may further comprise a membrane disposed over the mesh. The membrane may be elastic and may conform to the self-expanding mesh. The membrane may have an outer surface that substantially matches the native valve treatment site shape in the expanded configuration, and the membrane may form the central lumen. The membrane may comprise a resilient polymer, and the polymer may be impermeable to blood.

The personalized prosthetic valve may further comprise one or more radiopaque markers coupled to the membrane or the self-expanding mesh for facilitating implantation of the personalized prosthetic valve at the native valve treatment site. The prosthetic valve may also comprise one or more apertures extending through a sidewall of the personalized prosthetic valve. The one or more apertures may be fluidly coupled with the central lumen to allow blood flow or other fluids to flow between the central lumen and the one or more apertures. The one or more apertures may be configured to accommodate side branch vessels or other body passages such that the personalized prosthetic valve does not obstruct blood flow or fluid flow therethrough.

The native valve treatment site has a shape, and the lumen has a shape that substantially matches the shape of the native valve treatment site. The lumen may not substantially alter blood flow path across the treatment site. The lumen may have a cylindrical shape.

In still another aspect of the present invention, a personalized prosthetic valve for implantation at a native valve of a patient comprises a self-expanding membrane having a collapsed configuration and an expanded configuration. The collapsed configuration is adapted to be delivered to the treatment site, and the expanded configuration is adapted to expand the personalized prosthesis into engagement with the treatment site. The membrane in the expanded configuration is personalized to match the native valve, and the membrane has an outer surface that substantially matches the native valve shape and size in the expanded configuration. The membrane forms a central lumen configured to allow blood or other body fluids to pass therethrough.

The prosthetic valve may further comprise a plurality of valve leaflets coupled to the self-expanding membrane that have an open configuration and a closed configuration. In the open configuration the blood or the other body fluids are free to pass through the personalized prosthetic valve. In the closed configuration the plurality of leaflets are closer toward one another than in the open configuration, and the blood or the other body fluids are prevented from flowing upstream through the prosthetic valve.

In another aspect of the present invention, a method for manufacturing a personalized prosthetic valve comprises providing one or more images of a native valve, creating a digital data set characterizing shape and size of the native valve based on the one or more image, and transforming the digital data set into machining instructions. The method also comprises forming a mandrel using the machining instructions, wherein the mandrel has a shape that substantially matches the native valve, applying a mesh to the mandrel, and heat treating the mesh while the mesh is disposed over the mandrel so that the mesh is biased to return to a shape matching the shape of the native valve thereby forming the personalized prosthetic valve. The valve has a contracted configuration and an expanded configuration. The valve is adapted to be delivered to the native valve in the contracted configuration, and the valve is biased to return to the expanded configuration, which has a shape substantially matching the native valve.

Providing the one or more images may comprise providing one or more images obtained with computerized tomography (CT), magnetic resonance imaging (MRI), x-ray, ultrasound, or angiography. Transforming the digital data set into machining instructions may comprise transferring the digital data set into a computer aided design or computer aided manufacturing (CAD/CAM) system. Forming the mandrel may comprise machining a piece of metal. Forming the mandrel may comprise forming the mandrel so as to be undersized relative to the native valve. The undersized mandrel accommodates for thickness of the mesh.

Applying the mesh to the mandrel may comprise slidably disposing the mesh over the mandrel. Applying the mesh to the mandrel may comprise wrapping a filament around the mandrel, or wrapping a preformed flat mesh around the mandrel. Heat treating the mesh may comprise heat treating a nitinol mesh.

The method may further comprise removing the mandrel from the mesh and recovering the mesh. The method may also comprise forming at least one side aperture in the personalized prosthetic valve that is configured to allow blood flow or other fluid flow therethrough. The method may comprise forming a membrane over the mesh thereby forming a cover over the personalized prosthetic valve. Forming the membrane may comprise attaching a polymer cover to the mesh or dip coating a polymer cover over the mesh.

The method may further comprise mounting the personalized prosthetic valve on a delivery catheter, cleaning the personalized prosthetic valve and delivery catheter, packaging the personalized prosthetic valve and delivery catheter, and terminally sterilizing the personalized prosthetic valve and delivery catheter. The method may comprise requesting verification that the shape of the personalized prosthetic valve is appropriate for implantation at the native valve before shipping the personalized prosthetic valve from a manufacturing facility. Verification may be performed by a physician, and verification may be performed over the Internet. The method may comprise shipping the personalized prosthetic valve to a hospital.

The method may further comprise mounting the personalized prosthetic valve on a delivery catheter, placing the personalized prosthetic valve and the delivery catheter in packaging, sterilizing the personalized prosthetic valve and the delivery catheter in the packaging, and requesting verification that the personalized prosthetic valve is appropriate for implantation at the native valve site before opening the sterile packaging. The verification may be performed by a physician over the internet. The method may further comprise removing the personalized prosthetic valve from the mandrel so that a central lumen extends through the personalized prosthetic valve. The native valve may be an aortic valve. Other valves are also contemplated such as mitral valves, tricuspid valves, pulmonary valves and other valves.

In still another aspect of the present invention, a method for treating a damaged or diseased native valve a treatment site comprises providing a personalized prosthetic valve having a central lumen, an expanded configuration and a collapsed configuration. The valve is biased to expand into the expanded configuration, and the valve is also personalized to match shape of the treatment site. The central lumen is configured to allow blood flow or other body fluids to pass therethrough. The method also comprises advancing the personalized prosthetic valve in the collapsed configuration to the treatment site, self-expanding the personalized prosthetic valve into the expanded configuration. The expanded configuration has a shape that substantially matches the shape of the treatment site such that the personalized prosthetic valve expands substantially into engagement with the native valve at the treatment site. The method also comprises reducing retrograde blood flow across the native valve.

The personalized prosthetic valve may comprise a self-expanding wire mesh surrounded by a polymer cover, or the valve may comprise a self-expanding wire mesh, or the valve may comprise a resilient polymer. The treatment site has a shape and the lumen may have a shape that substantially matches the shape of the treatment site. The lumen may have a cylindrical shape and the lumen may not substantially alter blood flow path across the treatment site.

Advancing the personalized prosthetic valve may comprise advancing the valve through a blood vessel. Radially expanding the prosthetic valve may comprise retracting a sheath away from the personalized prosthetic valve, thereby allowing the personalized prosthetic valve to self-expand into the expanded configuration. Reinforcing the tissue may comprise anchoring the personalized prosthetic valve to the tissue. The treatment site may comprise a native aortic valve, and reducing retrograde flow may comprise directing blood flow through a plurality of valve leaflets coupled to the personalized prosthetic valve. The plurality of valve leaflets may have an open configuration and a closed configuration. In the closed configuration the plurality of valve leaflets may be adjacent one another to prevent the retrograde flow, and in the open configuration the plurality of valve leaflets may be disposed away from one another and the blood flow may freely pass therethrough. The treatment site may comprise a native aortic valve.

Reinforcing the tissue may comprise anchoring the personalized prosthetic valve in the native valve. Anchoring the personalized prosthetic valve may comprise engaging barbs on the personalized prosthetic valve with the tissue. The personalized prosthetic valve may comprise one or more radiopaque markers, and the method may further comprise aligning the one or more radiopaque markers with one or more anatomical features at the treatment site. The implantable prosthetic valve may comprise one or more apertures in a sidewall thereof, and the method may comprise preventing obstruction of blood flow through the one or more apertures in the sidewall.

These and other aspects and advantages of the invention are evident in the description which follows and in the accompanying drawings.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The understanding of the features and advantages of the present invention will be obtained by reference to the following detailed description that sets forth illustrative embodiments, in which the principles of the invention are utilized, and the drawings of which:

FIGS. 12A-12F illustrate exemplary mesh patterns;

DETAILED DESCRIPTION OF THE INVENTION

The present invention will be described in relation to the deployment of the prosthesis in an aortic aneurysm. However, one of skill in the art will appreciate that this is not intended to be limiting, and the devices and methods disclosed herein may be used in other parts of the body such as in the hollow anatomical structures including ducts, vessels, organs, or any other part of the body where there is a need to reinforce a lumen, channel, or other body space, or to anchor a prosthesis in those locations.

Figure 1:
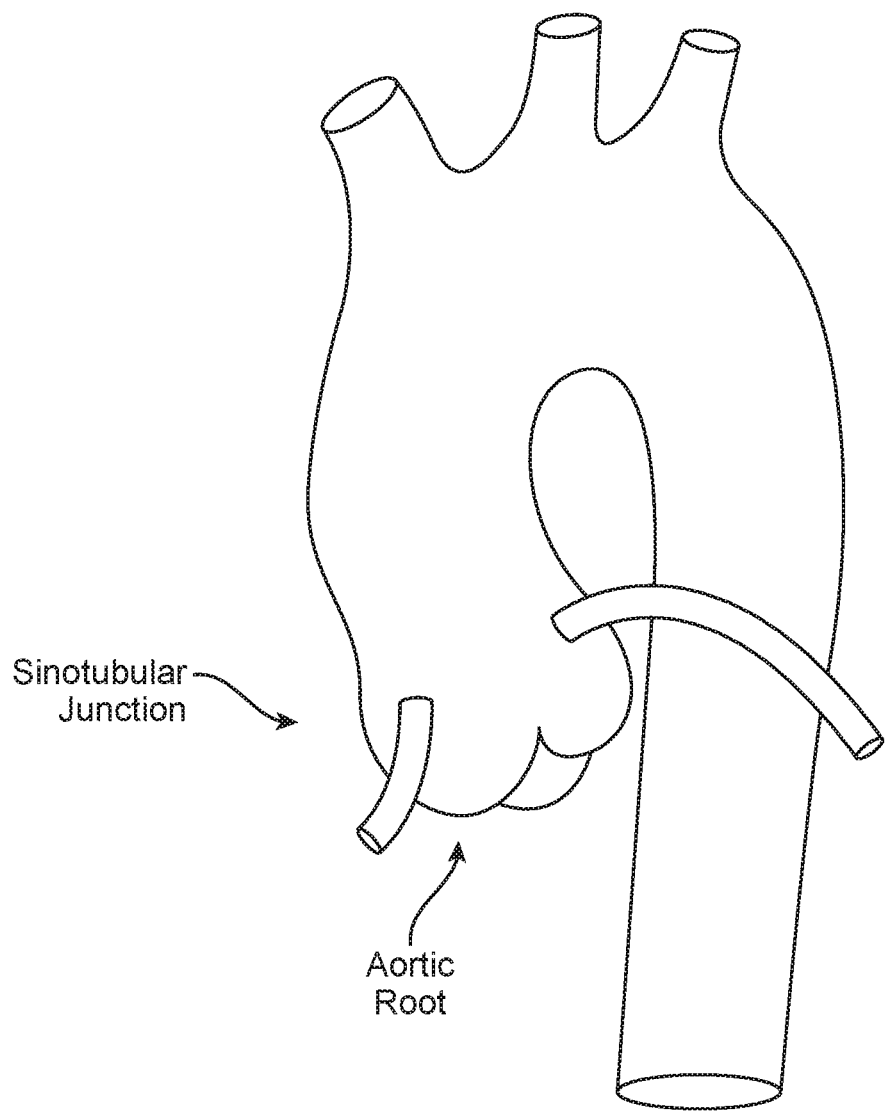
FIG. 1 Shows the schematic view of the aorta showing the aortic valve.

FIG. 1 shows the schematic view of the aorta from the aortic root to the thoracic portion of the descending aorta. The aortic valve is contained in the aortic root.

Figure 2:
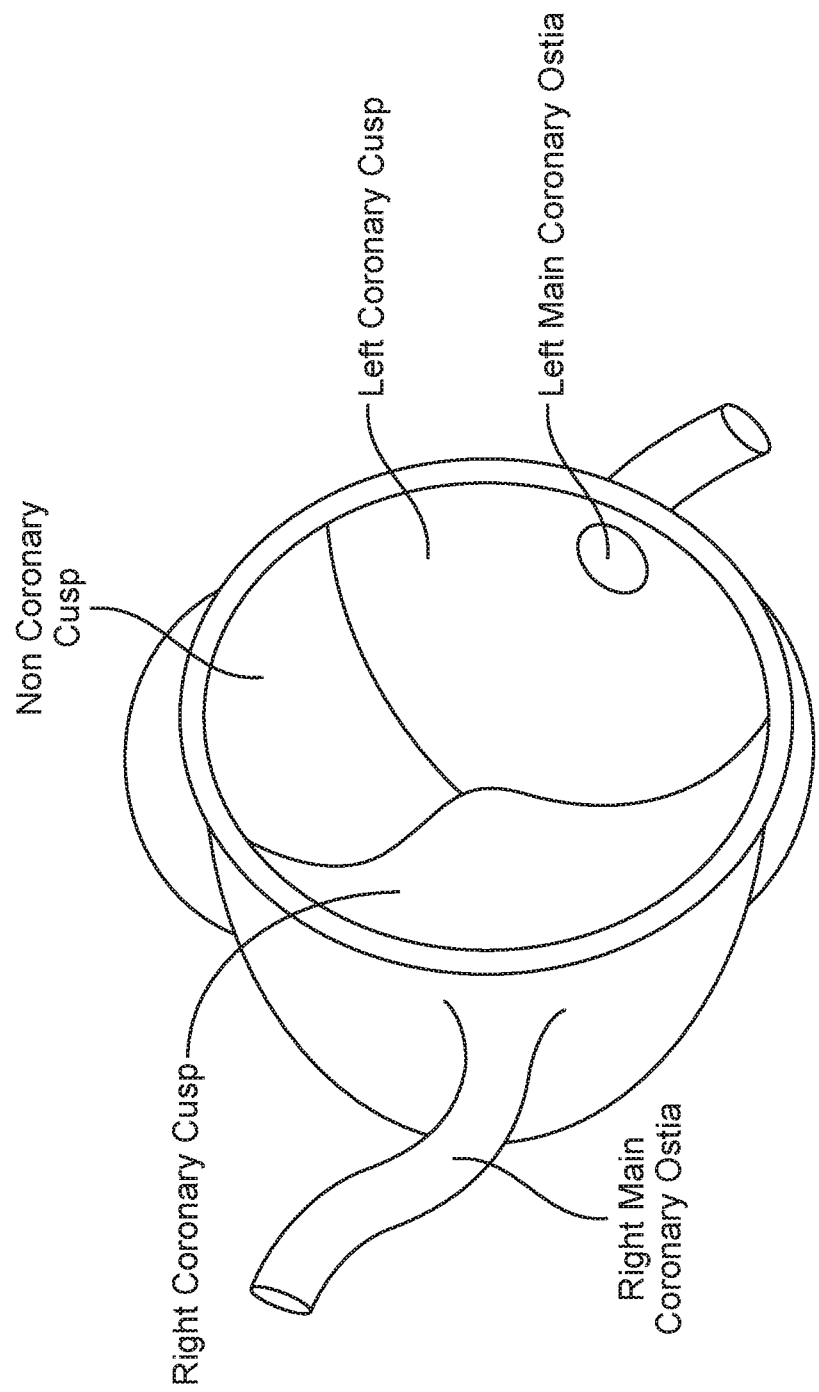
FIG. 2 Shows the cross-sectional view of the aortic valve at sinotubular junction.

FIG. 2 shows the cross section of the aorta at the root across the sinotubular junction. The aortic valve has a sinus which anatomically typically has three pockets where the valve leaflets reside. Two of the pockets contain the ostia for the coronary arteries.

Figure 3:
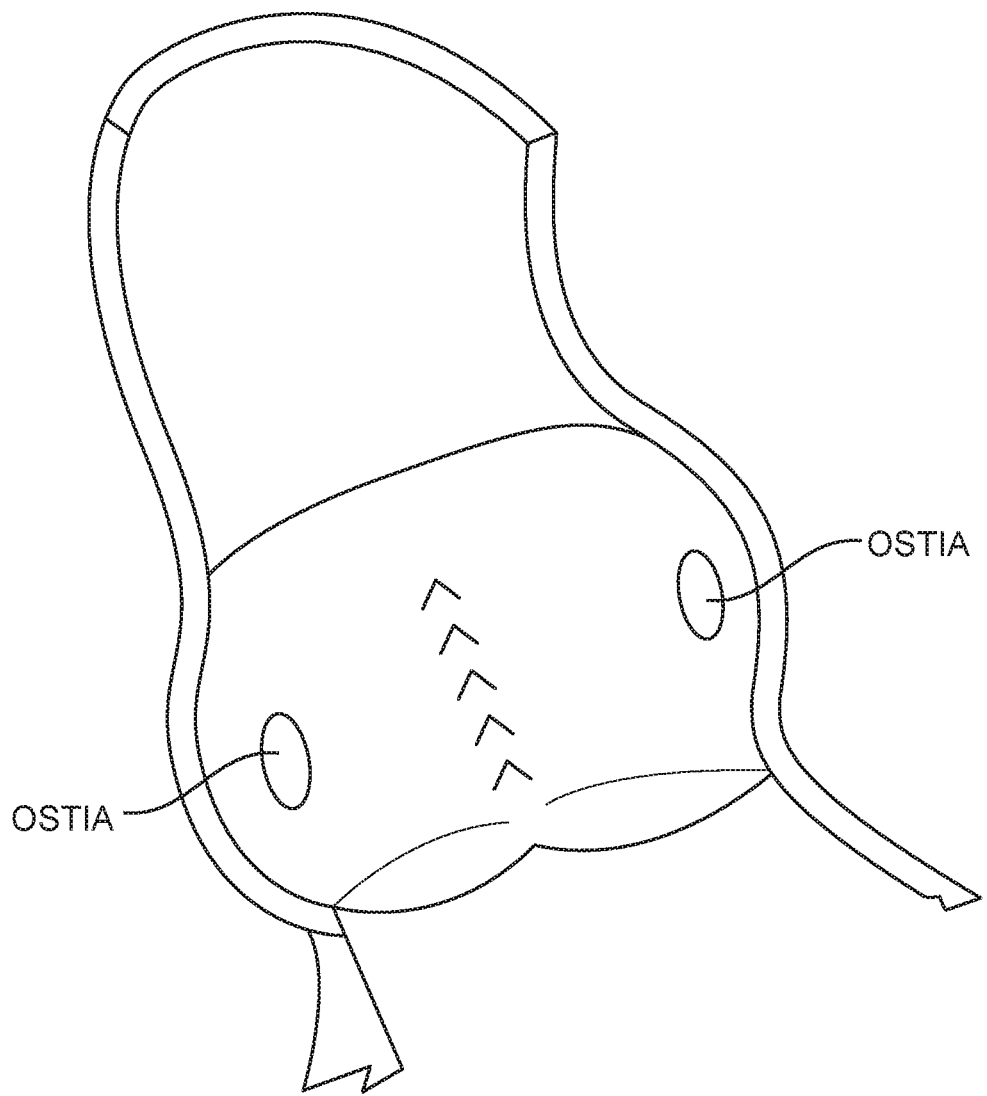
FIG. 3 Illustrates the aortic valve in a close up view with the valve leaflets removed for convenience.

FIG. 3 shows the close-up view of the sinus pocket of the aortic valve with the valve leaflets removed for convenience. It is situated just inferior to the sinotubular junction and joins the aorta to the left ventricle. It contains typically three bulbular pockets containing the leaflets. Two of the pockets contain the ostia for the coronary arteries.

Figure 4:
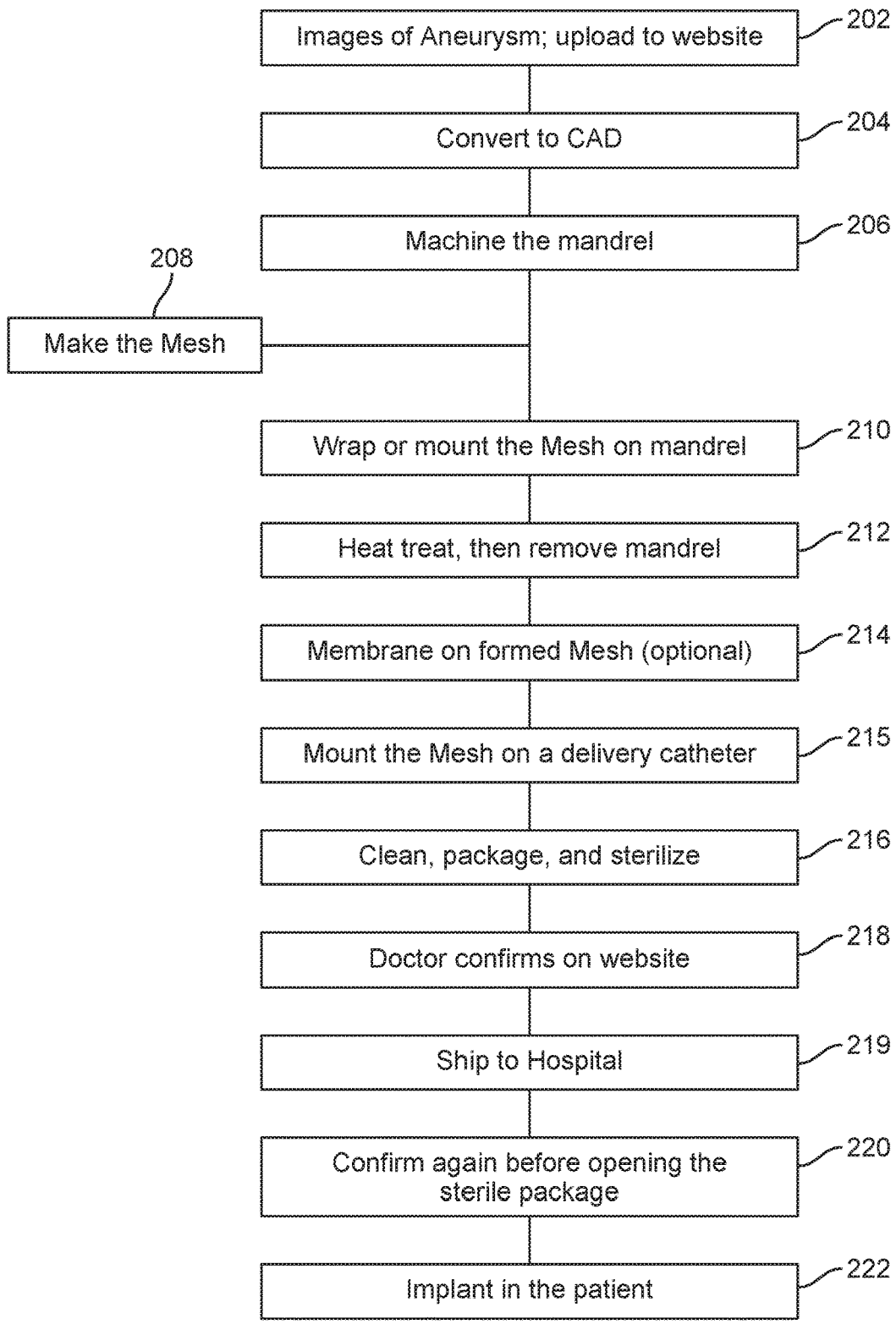
FIG. 4 Shows the flow diagram for the method of making the mesh for the aortic valve.

FIG. 4 shows a flow chart which illustrates an exemplary method of fabricating a personalized prosthesis that can be used to be implanted in the aortic valve region or any other treatment region. The method includes obtaining one or more images 202 of the treatment region which in this case is an aortic valve and surrounding blood vessel walls. These images may be obtained using computerized tomography (CT), x-ray, angiography, magnetic resonance imaging (MRI), ultrasound, or other imaging techniques known to those of skill in the art. The images may be stored on any storage media such as a CD-ROM, flash memory stick, etc., or the images may be stored in the cloud, on a remote server, or any other convenient and secure location. The images may be transferred to any of these locations using the Internet. Once the images are stored, the images or the digital data representing the images may be input 204 into a computer aided design/computer aided manufacturing (CAD/CAM) system. The CAD/CAM system then converts the images into a digital data set that can then be translated into machining instructions which are provided to a machining device such as a CNC lathe, mill, electrical discharge machine (EDM), etc. and the machining instructions are used by the machining device to machine 206 or otherwise form a mandrel or a mold having a shape that substantially matches the shape and volume of the treatment region. Alternatively, the image data can be used to construct a three dimensional model of the treatment region using the techniques such as 3-D printing. Thus the contours of the mandrel will match the contours of the treatment region, and the mandrel will substantially fill the volume of the treatment region, in this case, the aortic valve. The CAD/CAM system may be programmed to compensate for the thickness of materials that are applied to the mandrel later on, thus the mandrel may be slightly smaller than the actual size of the treatment region. Alternatively, the mandrel can be made of a size slightly larger so that the apposition of the mesh is more definitive against the wall of the cavity where the mesh is intended to be deployed. Although the mesh can be made smaller or larger proportionately in all dimensions, it would be more beneficial to make it larger or smaller in the radial dimension only. In other embodiments, the mandrel shape will match the contours of the treatment region without compensating for material thickness. In all cases, slightly smaller, exactly the same, or slightly larger size of the resulting mandrel shape substantially matches the treatment region shape and size, and the mandrel will substantially fill the volume of the treatment region.

Once the mandrel is formed, it can be used as a master mold from which a personalized prosthesis is fabricated. The personal prosthesis will then have a size and shape that substantially matches the treatment region which allows the personal prosthesis to anchor itself at the treatment region and prevent perivalvular leaks or movement of the mesh. A wire mesh is either pre-made 208 or otherwise provided. The mesh is preferably tubular and cylindrically shaped with both ends open so that the mesh may be slidably disposed over the mandrel like a sock, or in other embodiments the wire mesh may be wound 210 on the mandrel. The mesh and mandrel are then placed in a furnace, oven, salt bath, etc. to an elevated temperature for a desired time. The mesh and mandrel are then removed and cooled using a prescribed cooling procedure such as air cooling, quenching in oil or water, etc. This heat treats 212 the wire mesh and the wire mesh takes a set to the shape of the mandrel. Heat treating of metals, in particular self-expanding metals is known in the art. The formed mesh is then removed from the mandrel. In this embodiment, or any of the embodiments disclosed herein the wire mesh is preferably self-expanding, and may be made from metals such as superelastic nitinol, and thus the mesh will have an expanded configuration which matches the mandrel and hence also substantially matches the shape of the treatment region. When tension is applied to the ends of the mesh, the mesh will collapse into a collapsed configuration which has a lower profile and is suitable for loading onto a delivery catheter for endovascular delivery to the treatment region. The wire mesh in this or any of the embodiments described herein may also be a shape memory alloy such as nitinol such that placement of the mesh in a patient's body heats the mesh above a transition temperature and causes the mesh to radially expand outward.

Once the wire mesh has been heat treated to effect a shape, a fabric or polymer coating may be applied 214 to the bulbular region of the wire mesh. This will allow for a seal against the inside wall of the valve thus preventing the perivalvular leaks. The coating may be Dacron® polyester, expanded polytetrafluorinated ethylene (ePTFE), silicone, polyurethane, or other materials known in the art. The coating may be a sheet or tube of the material coupled to the mesh with adhesives, sutures, encapsulation, etc., or the mesh may be dip coated in order to apply the polymer to the mesh. The coating is preferably biocompatible and impermeable to blood or other body fluids. It may also be biodegradable and be made of materials such as polylactic acid (PLA) or polyglycolic acid (PGA). The resulting wire mesh with polymer coating forms a personalized implantable prosthesis having a shape that matches the treatment region and substantially fills the volume of the treatment region, in this case, the aortic valve. In other embodiments, the wire mesh remains uncoated and uncovered and forms the personalized prosthesis. Over course of time, the wire mesh surface will get endothelialized and will become imbedded in the wall of the valve. The personalized implantable prosthesis is then coupled to a delivery system 215 such as a delivery catheter, and the system is then cleaned, packaged, and terminally sterilized 216 using manufacturing processes known to those of skill in the art. For example, packaging may comprise placing the prosthesis in a procedure tray and sealing the tray with a Tyvek® lid, and terminally sterilizing the prosthesis may comprise gassing the prosthesis with ethylene oxide, autoclaving it with steam, or irradiating it with gamma or electron beam irradiation. In alternative embodiments, the coating may be applied directly to the mandrel without the mesh, thereby forming the prosthesis.

In some embodiments, the physician optionally may then confirm 218 that the resulting personal prosthesis is indeed the correct one for a particular patient prior to shipping the prosthesis from the factory. The verification may be conducted visually over the Internet by verifying size, shape, or dimensions of the prosthesis. Once the verification is complete, the personal prosthesis may be shipped 219 from the manufacturing facility to the doctor at a hospital, surgicenter, clinic or other place of business. Once received, the doctor or an associate may then optionally re-verify 220 that the prosthesis is the correct size and shape for the patient prior to opening up the sterile package. If the prosthesis is incorrect, it may be returned to the manufacturing facility. Verification may be accomplished by scanning a bar code and/or using the Internet. Once verification is complete, the personal prosthesis may be implanted 222 in the appropriate patient. One of skill in the art will also appreciate that appropriate patient privacy must be maintained during the entire personalized manufacturing process as required by the Health Insurance Portability and Accountability Act (HIPAA).

One desirable aspect of the present invention is to make the mesh matching the shape of the aortic valve and to have the anatomically accurate openings in the said mesh for the coronary artery ostia. The structure and method of making the same is described below.

Figure 5:
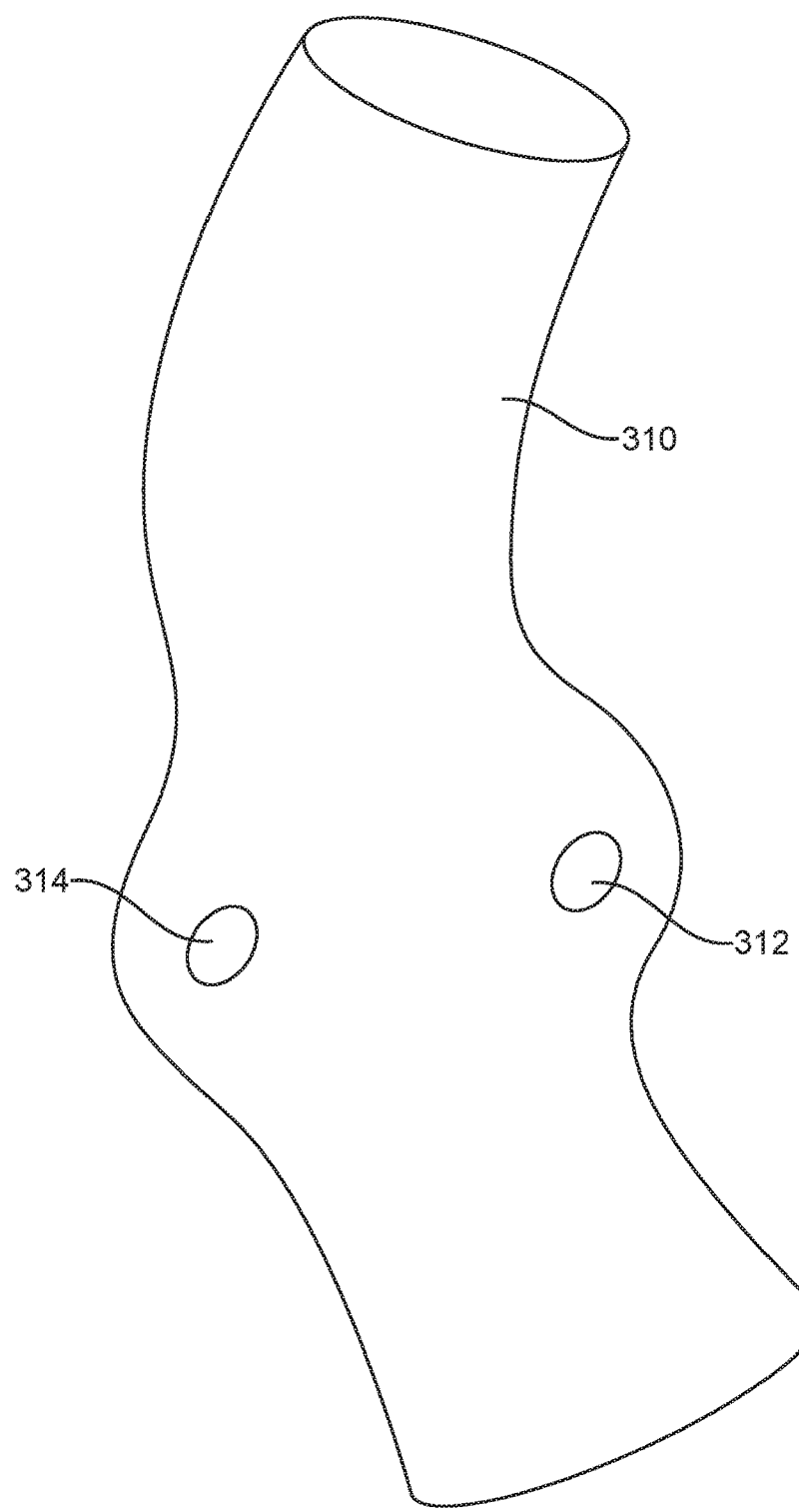
FIG. 5 Shows the mandrel matching the shape of the aortic valve.

FIG. 5 shows the mandrel 310 made to match the shape and size of the aortic valve. The figure also shows the holes 312 and 314 in the mandrel matching the locations of the coronary artery ostia. The locations of the apertures are accurately determined based on the image obtained, such as the CT scan and the like. The holes 312 and 314 are made by drilling into the mandrel or may be made as tapped holes. The intended function of the holes is to allow the attachment of pins or screws after the mesh has been mounted on the mandrel 310.

Figure 6:
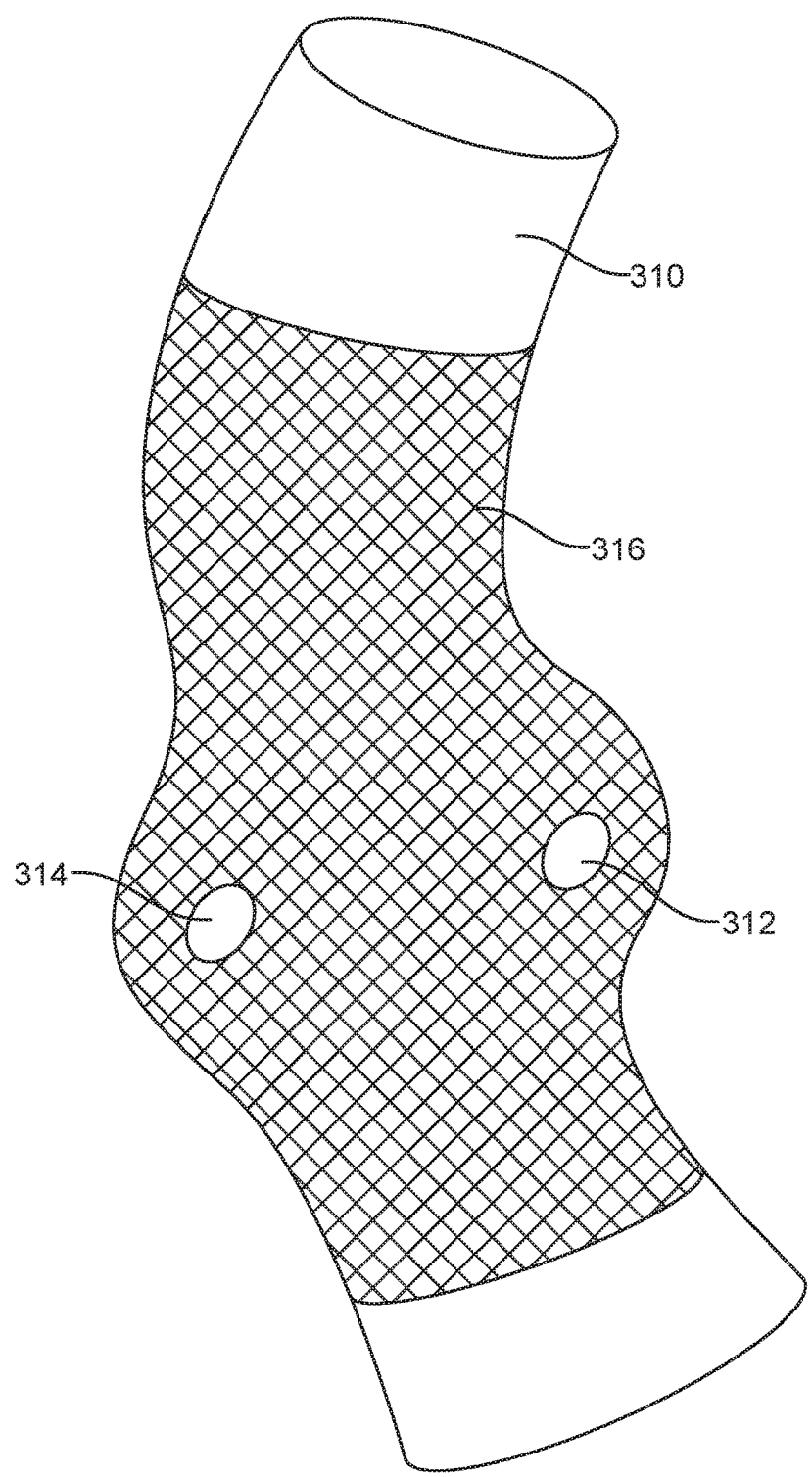
FIG. 6 Shows the mesh conformally over the mandrel.
Figure 6A:
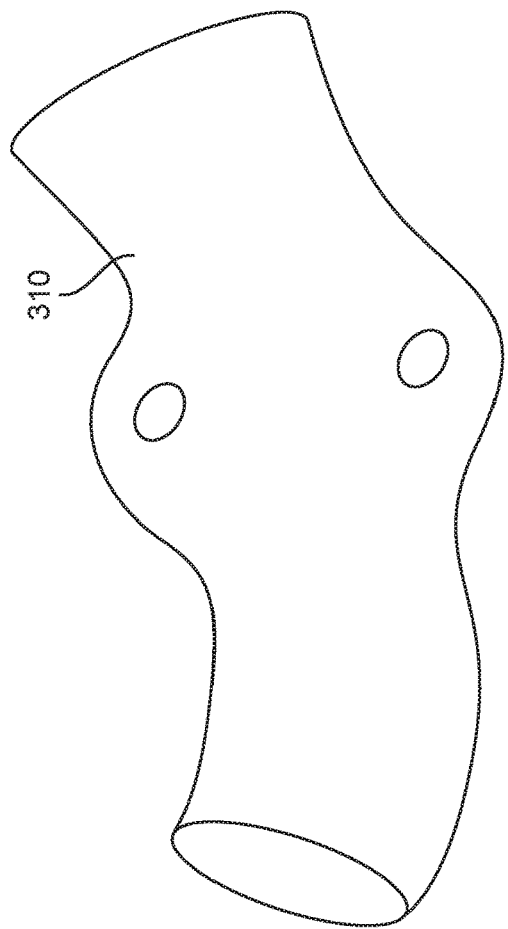
FIGS. 6A-6D illustrate exemplary methods of fabricating a personal prosthesis for the aortic valve.
Figure 6A:
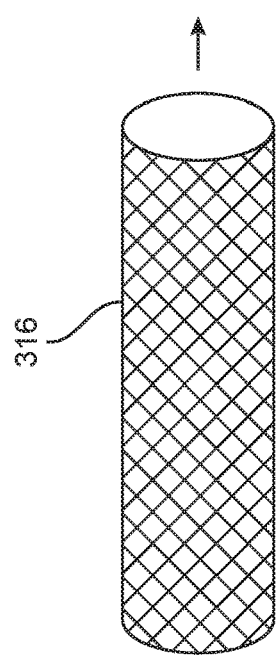
Figure 6D:
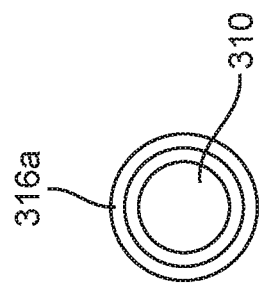
Figure 6C:
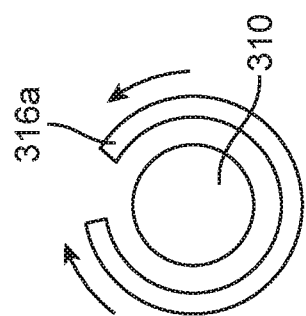
Figure 6B:
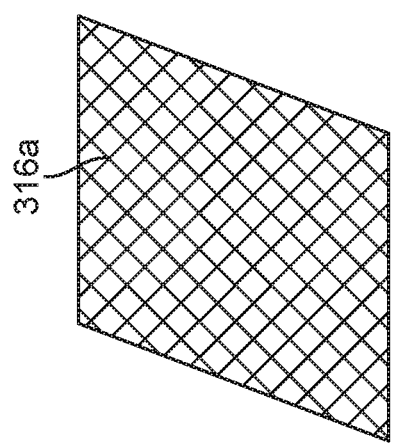

FIG. 6 shows the mandrel 310 with the mesh 316 disposed thereon. The wire mesh 316 may be pre-fabricated into a tubular sock-like shape that can be easily placed over the mandrel as seen in FIG. 6A, or in other embodiments, the wire mesh may be wound and formed over the mandrel. In still other embodiments, such as seen in FIGS. 6B-6C, a flat preformed mesh 316a (best seen in FIG. 6B) may be wrapped around the mandrel 310 as seen in FIG. 6C. Once wrapped, the edges of the flat mesh may be affixed to one another using methods known in the art such as welding, suturing, tying, bonding, soldering, etc. The mesh is then circumferentially disposed around the mandrel as seen in FIG. 6D. A ribbon, wire, or other filament may be wrapped over the mesh to ensure that it contacts the mandrel. FIG. 6 illustrates the wire mesh disposed over the mandrel in a manner described above.

Figure 7:
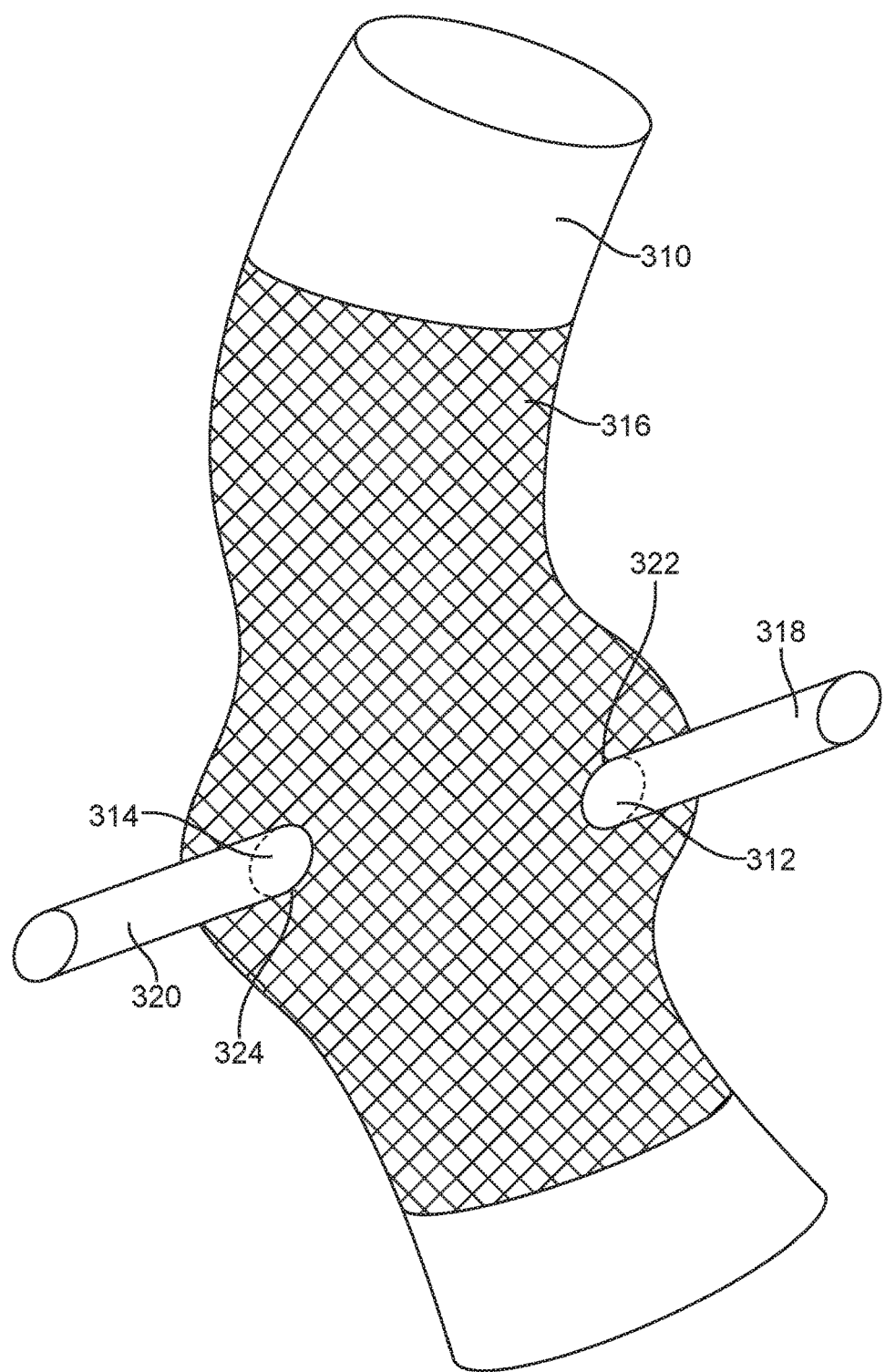
FIG. 7 Illustrates the method of making the openings in the mesh matching the coronary ostia.

Now referring to FIG. 7, the fenestrations (openings) in the mesh are made using the pins 318 and 320. Pin 318 is inserted or screwed in to the receiving hole 312 (FIG. 5) while displacing the intervening wires, such that the wires of the mesh are disposed around the pin 318 creating a fenestration 322 Similarly pin 320 is placed in hole 314 (FIG. 5) creating the fenestration 324.

Figure 8:
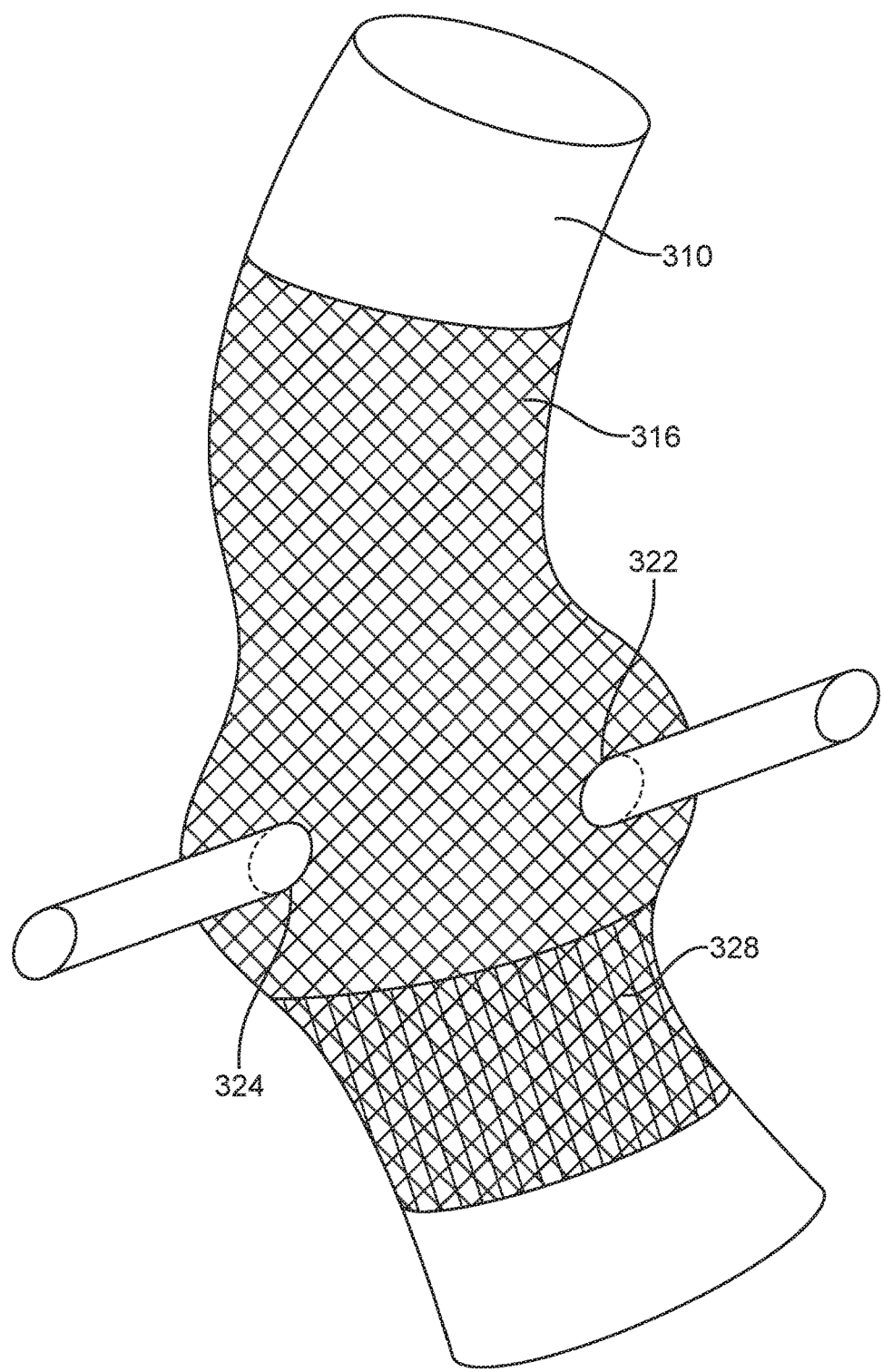
FIG. 8 Shows the mesh with coronary ostia on the mandrel.

The mandrel and mesh along with the fenestrating pins are then heat treated as described previously so that the wire mesh takes a set to the shape of the mandrel. The resulting mesh-on-mandrel is shown in FIG. 8 with the pins still in place. After heat treatment is completed, a portion of the mesh and mandrel may be dip coated with a polymer, or the polymer or fabric cover 328 may be applied to the lower portion of the mesh 316, as shown in FIG. 8, using methods known to those of skill in the art. The polymer or fabric cover 328 is preferably impermeable to blood to prevent blood from flowing across the wall of the prosthesis. The covered portion of the mesh, when appositioned against the corresponding inner wall of the valve, provides for the sealing of the mesh so that the problem of perivalvular leak is mitigated. Alternatively, the entire mesh may be covered with a membrane covering such as a dip-coated polymer or otherwise applied polymer or fabric. The fenestrations 322 and 324 can be made by removing the membrane from the site of said fenestrations by cutting, punching, dissolving, or other means known in the art. Alternatively, the coating 328 can be disposed on a portion or the whole mesh 316 after it has been removed from the mandrel. The fenestrations 322 and 324 can then be created as described above.

Figure 9:
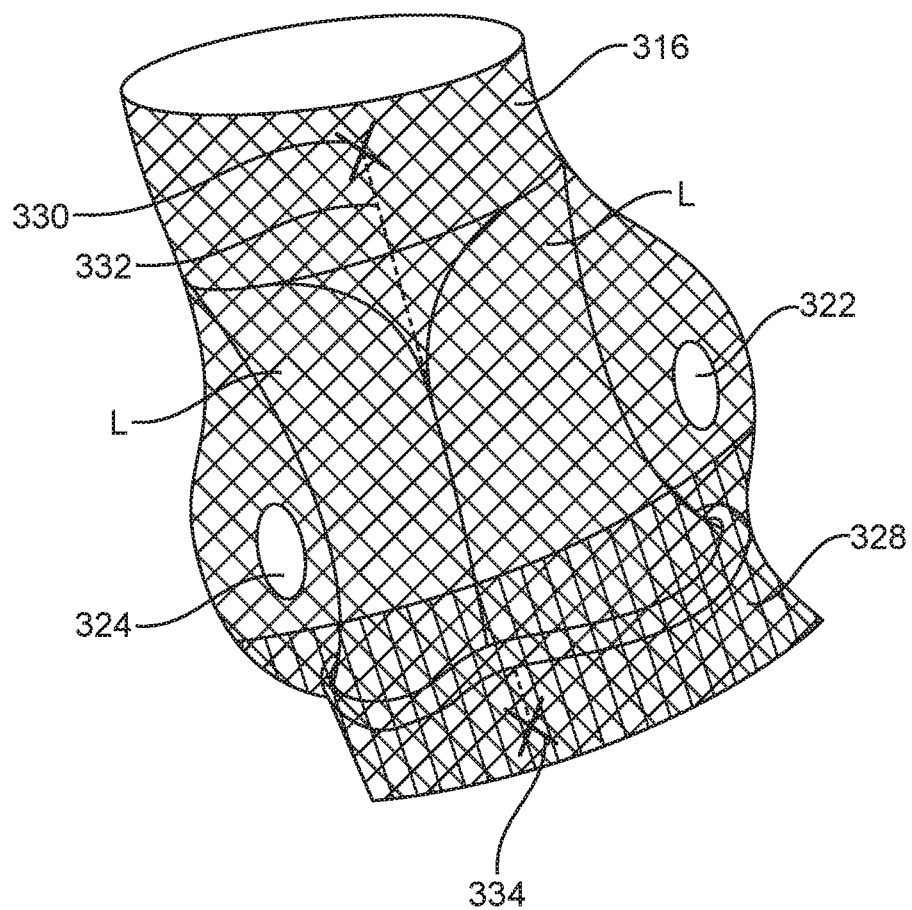
FIG. 9 Shows the personalized finished mesh with alignment markers for the aortic valve.

FIG. 9 shows the finished mesh 316 which is disposed with the fenestrations 322 and 324 which match with the corresponding ostia of the coronary arteries. One or more location markers such as radiopaque markers 330, 332, and 334 markers are optionally attached to the polymer or fabric cover and/or to the wire mesh. The locations of the markers are selected based on the anatomical information obtained from the corresponding image scan such as the CT scan. The said location may be a certain rib, vertebrae and the like. The markers 330, 332, and 334 are used for accurate alignment of the mesh in the aortic valve cavity. All or portion of the mesh 316 may be dip coated with a polymer, or the polymer or fabric cover 328 may be applied to the lower portion of the mesh 316. Prosthetic valve leaflets may be coupled to the internal portion of the mesh thereby forming a prosthetic valve that permits antegrade blood flow and prevents retrograde blood flow. The leaflets L may form a bicuspid or tricuspid valve, or other configurations of leaflets may also be employed. The leaflets may be synthetic material such as ePTFE, Dacron, or other materials may be used such as pericardial tissue.

Figure 10:
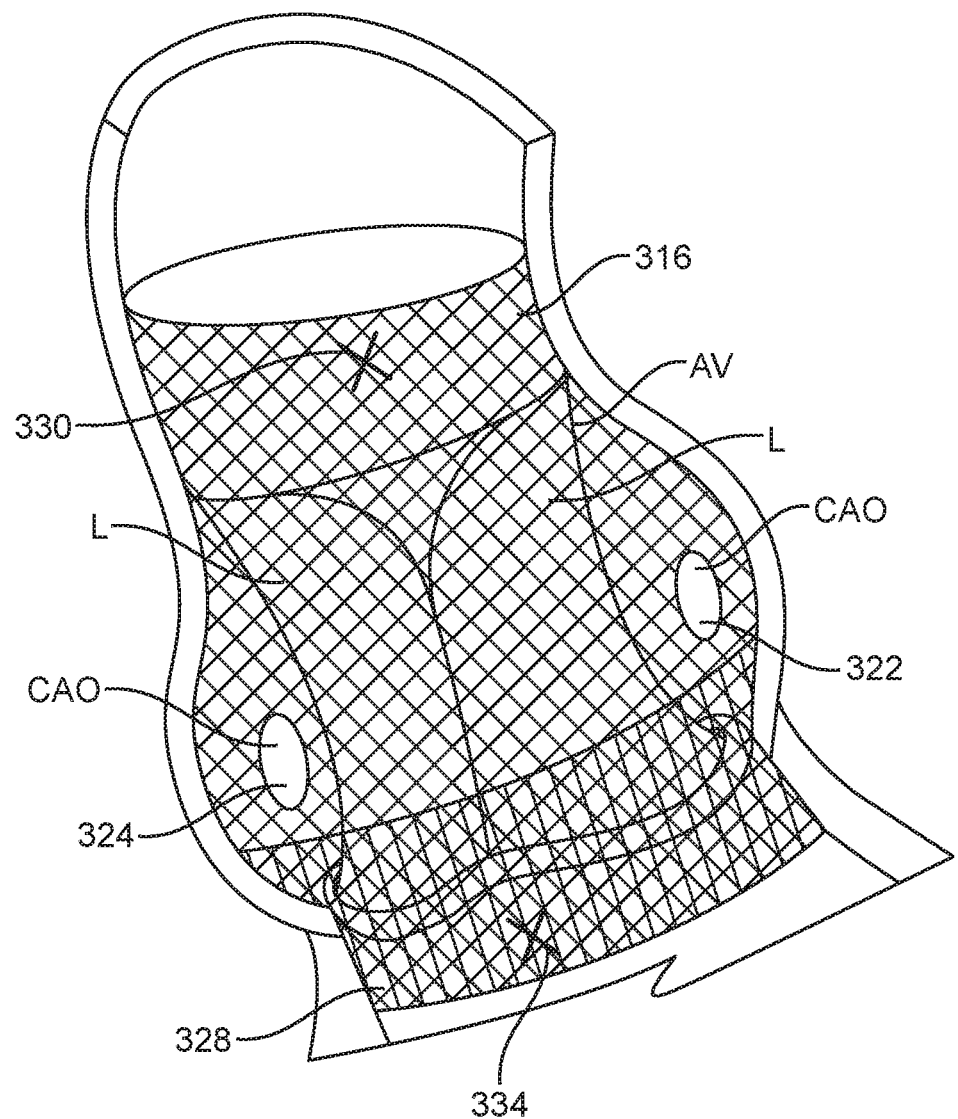
FIG. 10 Shows the personalized mesh deployed in the aortic valve cavity.

FIG. 10 shows the mesh 316 positioned in the aortic valve cavity AV in anatomical alignment. The mesh has expanded into position such that the outer surface of the mesh substantially engages and conforms to the inner surface of the native valve and adjacent tissue such as the vessel walls. Thus, the prosthetic valve is in engagement with the native tissue and this helps to prevent perivalvular leakage around the prosthesis. Additionally, fenestrations 322, 324 are aligned with the native coronary artery ostia, thus blood flow to the coronary artieries remains substantially unobstructed. The prosthetic valve may be delivered and aligned with the native valve anatomy and coronary artery ostia CAO by visualization of the radiopaque markers 330, 334.

Figure 11A:
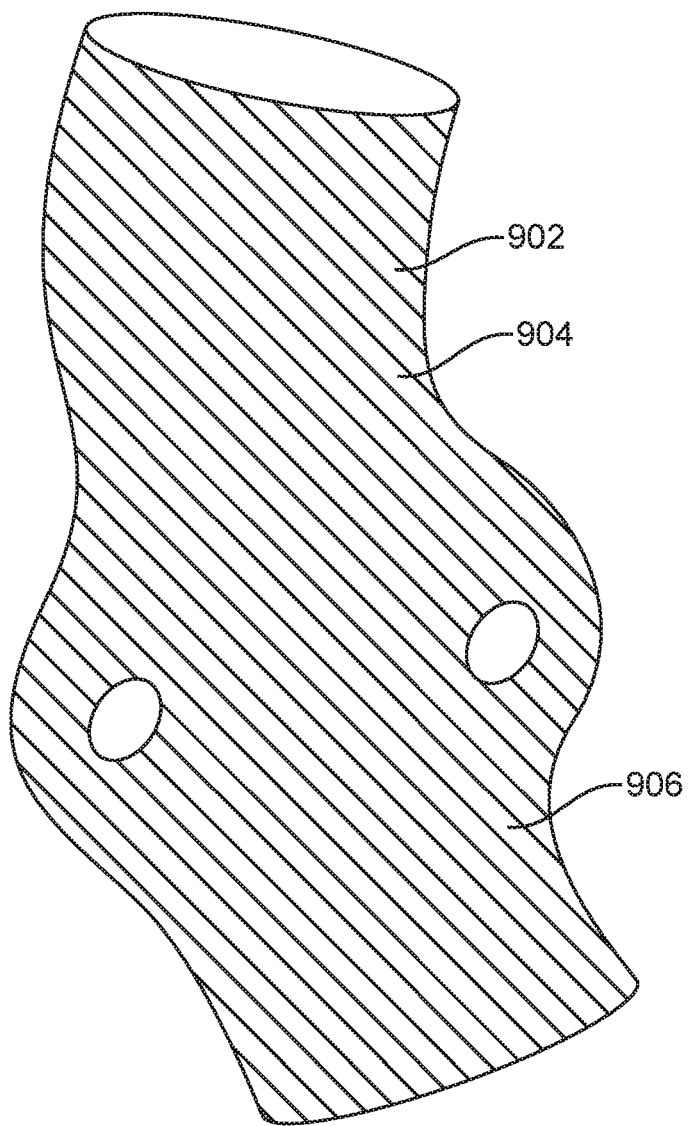
FIGS. 11A, 11B illustrate exemplary mesh patterns.
Figure 11B:
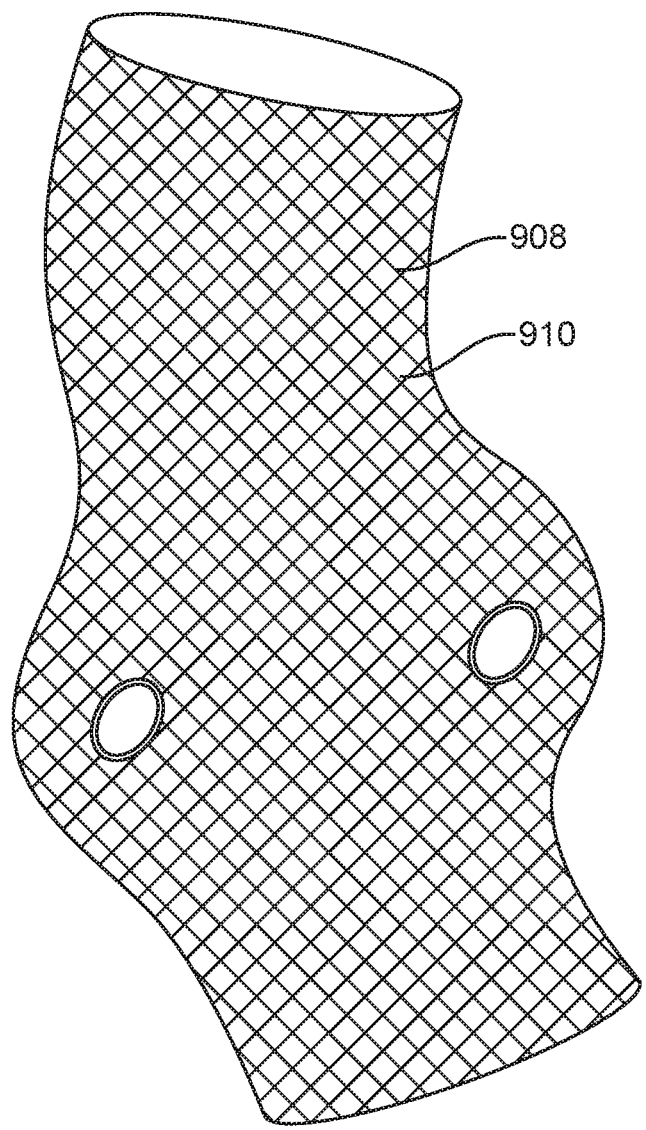

The personalized prostheses described above preferably include a wire mesh that self-expands to the personalized shape. Various wire patterns may be used to create the mesh. For example, FIG. 11A illustrates a mesh 902 having one or more filaments 904 which are spirally wound and an optional polymer or fabric cover 906 is applied to the mesh. This pattern of forming the mesh is advantageous because there is no overlap of the filaments, and the spiral pattern helps the mesh to be collapsed into a low profile for delivery. FIG. 11B shows the mesh 908 made of the filaments 910 in the form of a braid and an optional polymer or fabric cover 910 is applied to the mesh.

Figure 12A:
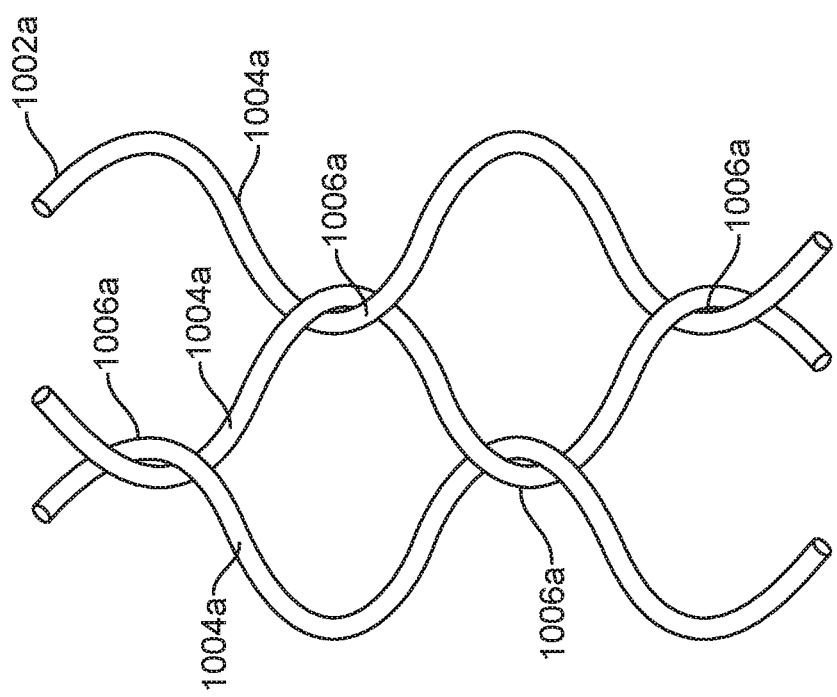

FIGS. 12A-12F illustrate other exemplary mesh patterns. FIG. 12A illustrates a mesh 1002a having one or more filaments 1004a that interweave with one another similar to traditional fencing wire or chicken wire, to form a single overlapping or twisted region 1006a. The overlap region is preferably in every row and every column of the mesh where the filaments meet. The overlapping region forms a protuberance which may be advantageous since the protuberance may help embed the prosthesis into the tissue at the treatment site thereby helping to anchor the prosthesis. Having a single overlap of the filaments helps the filaments move relative to one another thereby allowing the prosthesis to be easily collapsed which is desirable during loading onto a delivery system and also helps to keep the profile of the prosthesis minimal. This is also advantageous since it allows the prostheses to expand and collapse in concert with the pulsatile nature of the blood as it flows through the aorta or other vessel. However, in some circumstances, the single overlapping or twisted region may not be secure enough to keep the mesh in its formed pattern or to provide adequate support to the aneurysm, especially when the prosthesis is under tension or compression because the wires in the mesh may slip or slide relative to one another. The prosthesis undergoes tension and compression during loading on a delivery system, during deployment, and after implantation due to the pulsatile nature of blood flow.

Figure 12B:
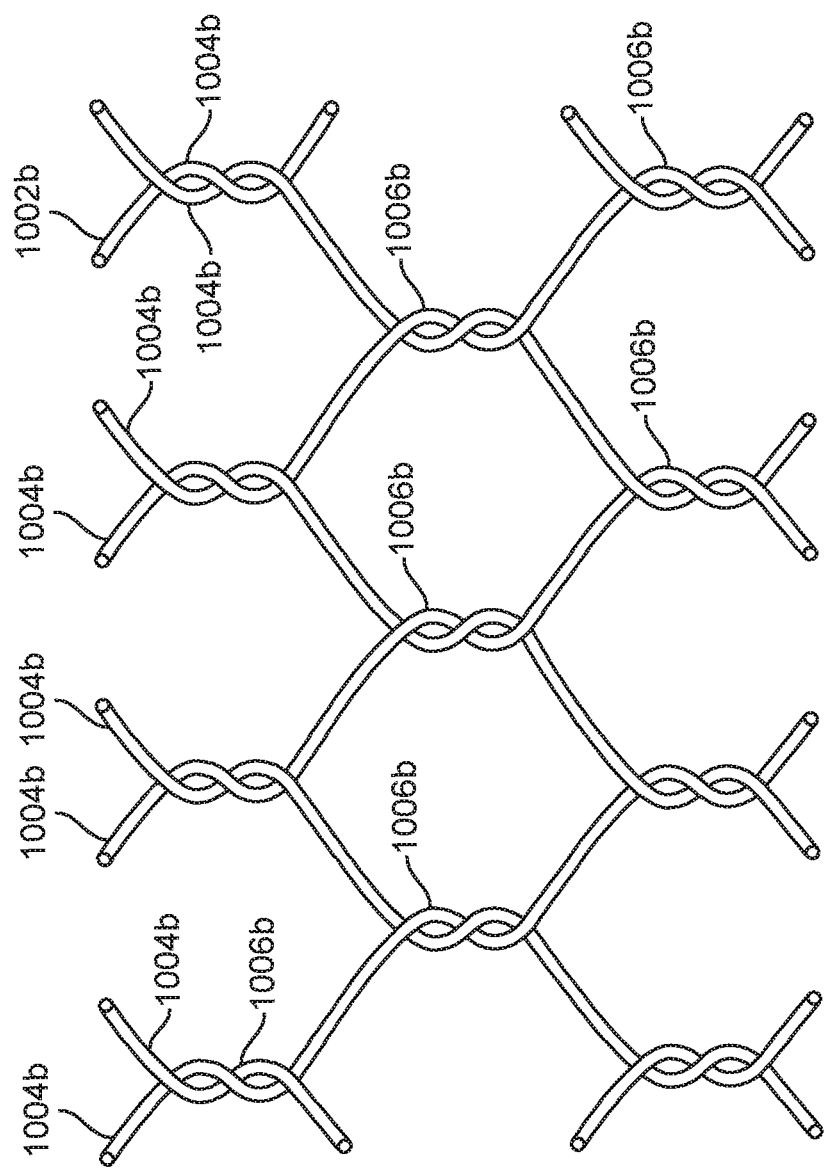

FIG. 12B illustrates an alternative embodiment of a mesh pattern that is more secure than the embodiment of FIG. 12A. Mesh 1002b has one or more filaments 1004b that interweave with one another to form a double overlapping or twisted region 1006b. The overlap region is preferably in every row and every column of the mesh where the filaments meet. The overlap region forms a protuberance similar to that in FIG. 12A and thus may also be useful in anchoring the prosthesis. Having the double overlapped or twisted region secures the filaments together more tightly and thus helps prevents the filaments from slipping or sliding relative to one another when the prosthesis is under tension or compression. Thus the prosthesis retains its shape and provides more support than the embodiment in FIG. 12A. However, in some circumstances, the wires may still slip or slide relative to one another, thus further securing of the filaments may be needed.

Figure 12C:
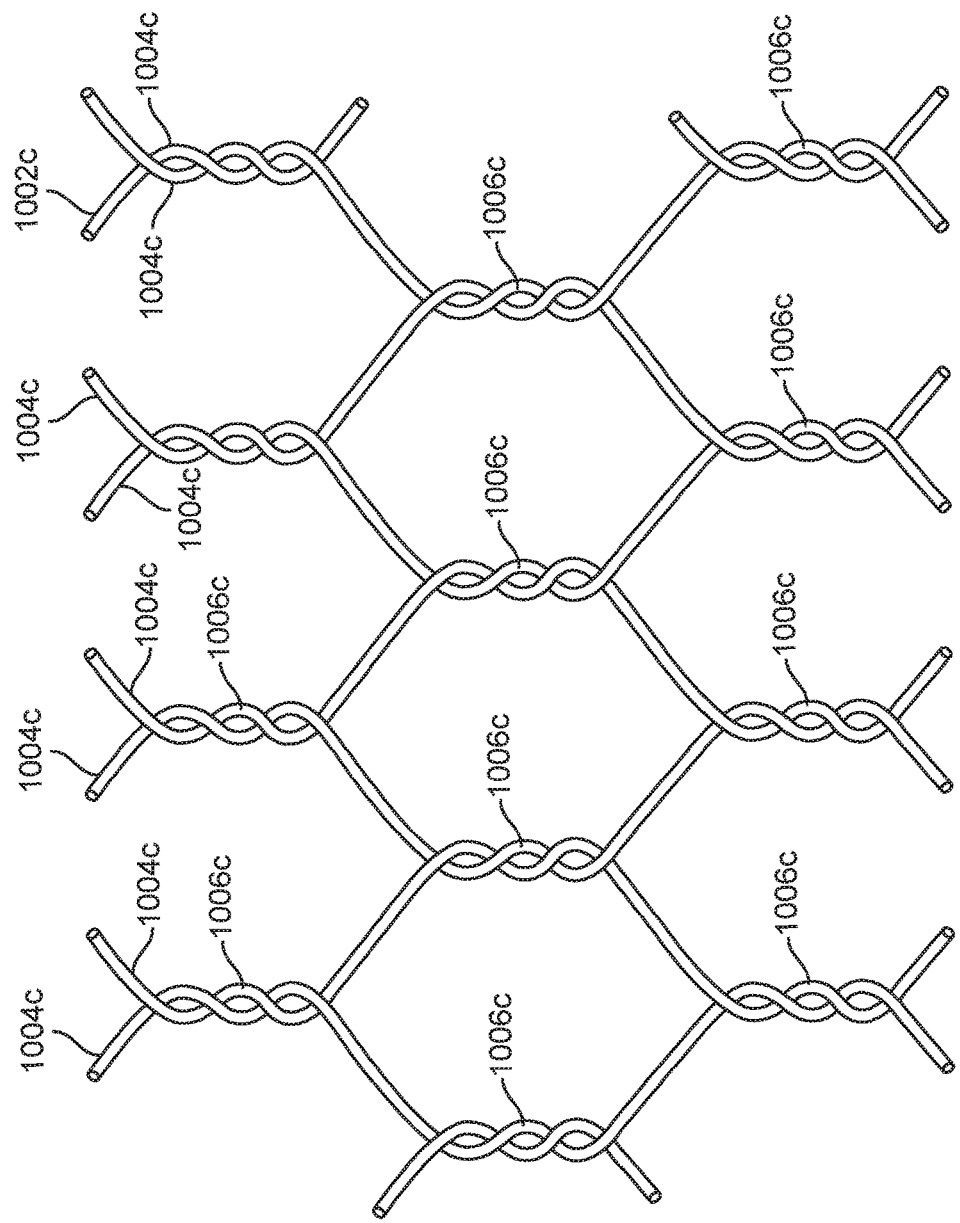

FIG. 12C illustrates still another embodiment of a mesh pattern which helps provide a stable mesh. The mesh 1002c has one or more filaments 1004c that interweave with one another to form a triple overlapping or twisted region 1006c. The overlap region is preferably in every row and every column of the mesh where the filaments meet. The overlap forms a protuberance similar to those previously discussed and therefore may aid in anchoring of the prosthesis. Having the triple overlap or twisted region secures the filaments together even more tightly than in the previous embodiments and thus the filaments are further constrained from slipping or sliding relative to one another when the prosthesis is under tension or compression. In some circumstances, having the triple overlap region secures the filaments together tightly enough that they cannot move at all relative to one another when the prosthesis is under tension or compression. If the filaments cannot move at all relative to one another, this prevents the prosthesis from axially or radially expanding or contracting which interferes with its ability to be loaded in a collapsed configuration onto a delivery system, from expanding radially outward upon deployment, or from expanding and contracting in concert with the vessel wall due to pulsatile blood flow.

Figure 12D:
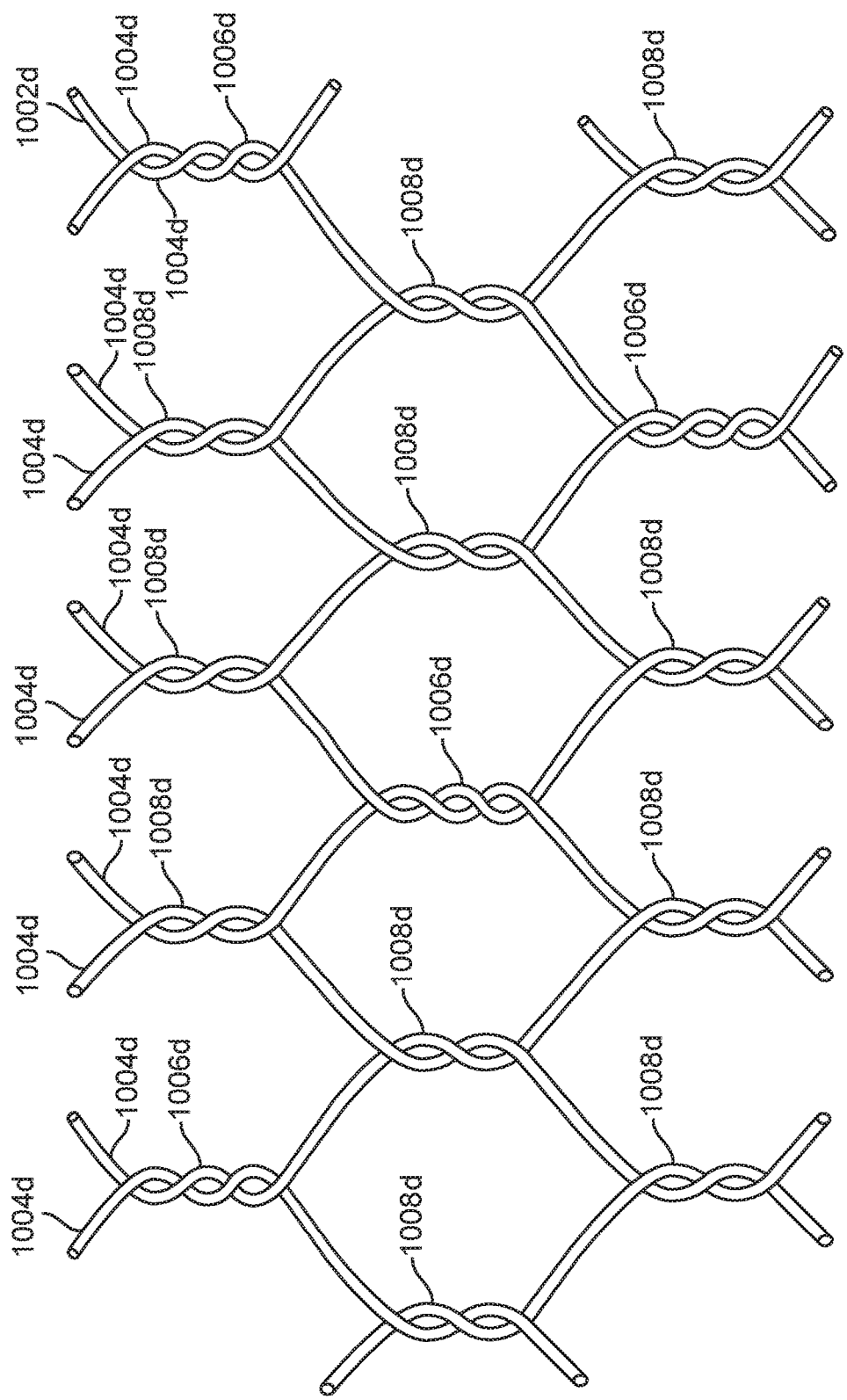

FIG. 12D illustrates a preferred hybrid embodiment of a mesh pattern that secures the filaments together securely so that the prosthesis holds its shape and provides good support during tension and compression, and yet at the same time still allows some movement between the filaments so that the prosthesis can expand and contract. Mesh 1002d has one or more filaments 1004d that interweave with one another to form an alternating pattern of a triple overlap or twisted region 1006d followed by a double overlap or twisted region 1008d, followed by another double or twisted overlap region 1008d, and then the pattern repeats. The pattern repeats so that everywhere the filaments overlap with one another, there is either a double or triple overlap or twisted region. The overlap region forms a similar protuberance as previously described which may be useful for anchoring the prosthesis. This hybrid weave has the advantages of both the double and triple overlap weaves previously described. Thus, the triple overlap regions secure the filaments together to minimize their movement relative to one another during compression or tension and thus the prosthesis holds its shape and provides good support, while at the same time the double overlap regions allow some movement of the filaments relative to one another thereby allowing the prosthesis to axially and radially expand and contract during delivery, deployment, and after implantation. The weave preferably minimizes or substantially eliminates axial expansion and contraction while allowing radial expansion and contraction.

FIGS. 12E and 12F illustrates expansion and contraction of a personalized prosthesis such as those described above using the weave of FIG. 12D. Without being bound by any particular theory, it is believed that the filaments will remain tightly engaged with one another when the prosthesis 1002d is under tension such as while the heart is in systole as seen in FIG. 12E and represented by arrows 1018d. Here, the filaments 1004d remain tightly wound together in both the double overlap region 1008d as well as the triple overlap region 1006d. The gap 1012d between adjacent filaments wound together in a region 1008d may be represented by distance S1 and the pitch 1010d or spacing between adjacent columns of wound filaments may be represented by distance P1 during systole. When the prosthesis is compressed such as when the heart is in diastole, as indicated by arrows 1020d in FIG. 12F, the pitch or spacing 1014d between adjacent columns of wound filaments generally decreases relative to the expanded configuration. Moreover, the gap 1016d between adjacent filaments wound together in a double overlap region 1008d increases when the prosthesis is in the expanded configuration thereby allowing the filaments to slide relative to one another. The gap between adjacent filaments wound together in a triple overlap region remain twisted together and there is substantially no relaxation. Thus, when viewing the prosthesis laying on its side with its longitudinal axis horizontal, the triple-double-double-double horizontal weave pattern accommodates the motion of the aorta vessel wall caused by the pulsatile motion of the blood flowing through it. Of course, one of skill in the art will appreciate that this particular pattern is not intended to be limiting. Other patterns may be used including any combination or permutation of the single, double, triple, or more than three overlapping regions.

Figure 13:
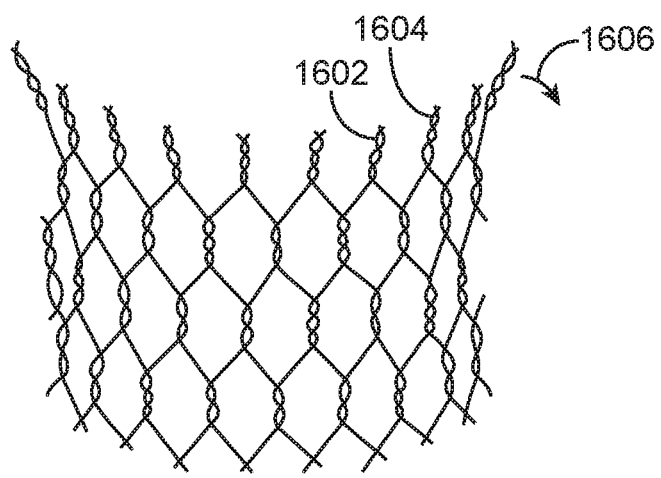
FIG. 13 illustrates an exemplary embodiment of an end of a prosthesis.

The filaments on the proximal and distal ends of the prosthesis may be terminated in any number of ways. FIG. 13 illustrates one exemplary embodiment. The prosthesis 1602 has the triple-double-double-double weave pattern of FIGS. 12A-12F described above. The filaments may terminate in an end region 1604 by twisting the filaments such that they overlap one another four times. One of skill in the art will appreciate that this is not intended to be limiting and the number of overlapping regions may be one, two, three, four, five, six, or more. Alternatively, the filament ends may be tied in a knot to prevent the filaments from unraveling. Additionally, the ends may remain extending axially outward to help anchor the prosthesis in tissue by partially piercing the tissue, or the ends may be formed into curves, loops, or other shapes to prevent sharp ends from protruding and causing tissue trauma. This prevents the filaments from moving relative to one another. Additionally, the end region 1604 may then be bent slightly radially outward 1606 to form a skirt or flanged region which flares outward and thus can embed into the vessel wall to help anchor the prosthesis.

Figure 14:
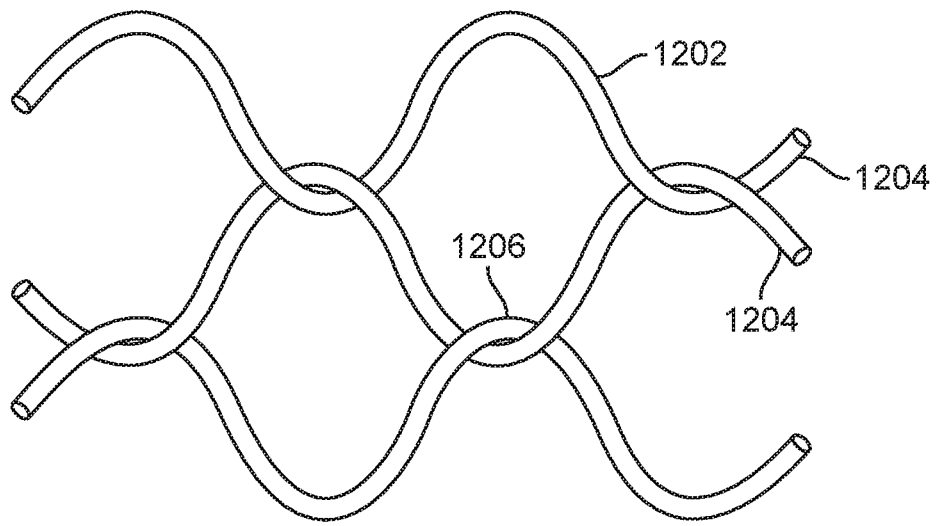
FIG. 14 illustrates an exemplary mesh.

In the embodiments of FIGS. 12A-12F, the weave pattern has been described when the prosthesis is sitting on its side such that the longitudinal axis of the prosthesis is generally horizontal. Thus, the weave pattern is generally parallel to the longitudinal axis, and the filaments are weaved together in a horizontal pattern across the prosthesis and with a vertical orientation. In still other embodiments, the weave pattern of FIGS. 12A-12F may be rotated ninety degrees so that the filaments are weaved an orthogonal direction. FIG. 14 illustrates an exemplary embodiment of the weave pattern in FIG. 12A rotated ninety degrees. The weave is illustrated with the prosthesis laying flat on its side with its longitudinal axis generally horizontal. Thus, mesh 1202 includes a plurality of filaments 1204 that are weaved together to form a single overlap or twisted region 1206. Other aspects of this embodiment generally take the same form as in FIG. 12A. The other embodiments described previously may also be weaved in a pattern that has been rotated ninety degrees. Any of the mesh patterns described herein may be formed into a round tubular member or the mesh may be woven into a flat sheet and the ends may be joined together to form a round tubular member. Additionally wires or filaments of different diameters may be combined with one other, or a single diameter may be used throughout a single mesh prosthesis in order to obtain desired mechanical properties.

Figure 15:
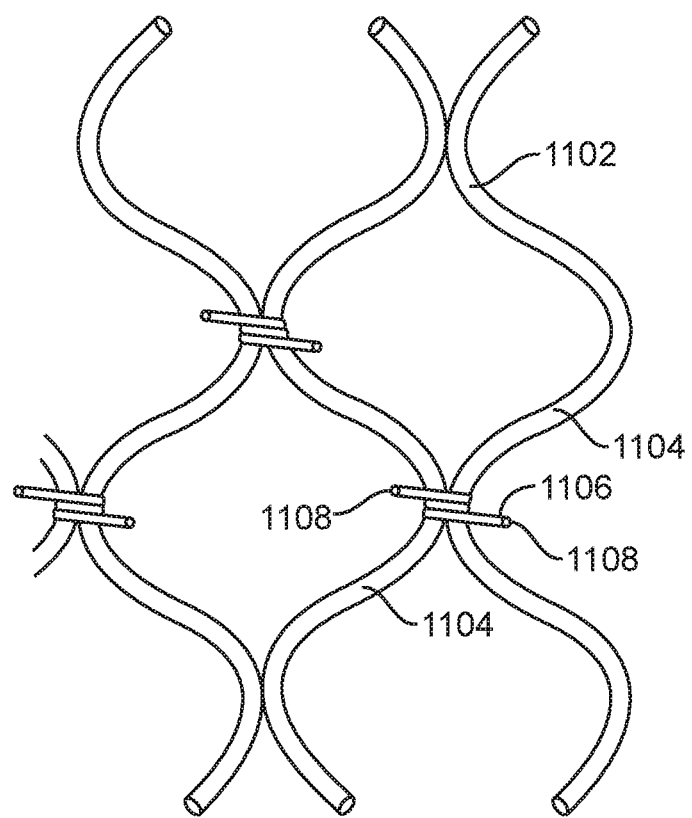
FIG. 15 illustrates another exemplary embodiment of a mesh pattern.

FIG. 15 illustrates still another pattern for the mesh 1102. This pattern has one or more filaments 1104 woven into an undulating pattern. Adjacent rows of the undulating filaments are tied together with a wire, suture, or other tie 1106. Optionally, one or both ends of the tie 1106 may be left uncut to form a barb 1108 that can also be used to help anchor the prosthesis to tissue at the treatment site. Any of these wire mesh patterns with anchoring or without anchoring may be used in any of the embodiments described herein.

Figure 16:
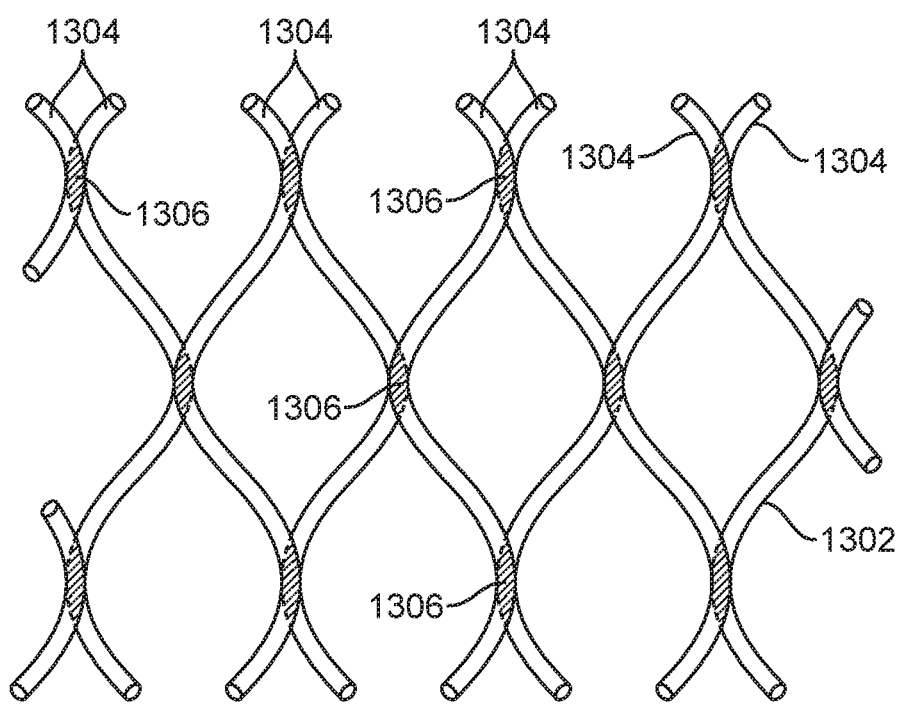
FIG. 16 illustrates yet another exemplary embodiment of the mesh.

FIG. 16 illustrates yet another exemplary embodiment of a mesh. The mesh 1302 includes one or more filaments 1304 which are formed into an undulating pattern having peaks and valleys. The peaks and valleys in one row of the mesh may overlap with the valleys and peaks of an adjacent row of the mesh. The overlapping portions may then be welded 1306 together to keep the filaments coupled together. In alternative embodiments, welds may be combined with any of the previous mesh embodiments.

One objective behind the placement of the mesh against the wall of the aortic valve pocket is to apposition the mesh so that the perivalvular leak is eliminated. In addition, the secure apposition of the mesh guards against any possible migration on the said mesh. After the mesh is decisively appositioned against the aorta wall, an endothelial lining will develop on the wire mesh over time, essentially imbedding the mesh in the tissue covering the wall of the lumen. This process is well documented in animal models (for example, ref. 'Time Course of Reendothelialization in a Normal Coronary Swine Model: Characterization and Quantification', A. Perez de Prado et al, Vetenary Pthology Online, Mar. 10, 2011; http://vet.sagepub.com/content/early/2011/03/10/0300985811400446) through the observations of the resident stents in the arteries, such as coronary and carotid, of the vasculature. The endothelialization process takes about two weeks or more, and within a few months, the wire mesh would be well imbedded in the wall of the lumen.

During the endothelialization process, the perivalvular leaks or migration of the mesh may occur. Thus it would be beneficial if the mesh, which is intended to be implanted in the aortic sinus pocket, is designed to be larger in size than the existing anatomical dimensions in the radial dimension to accommodate the possibility of the aortic sinus pocket changing shape during the course of endothelialization and imbedding. A mesh larger than the actual implant site anatomy in radial dimension has two main advantages. First, the apposition of the mesh against the wall of the aorta is more decisive at the time of deployment. Secondly, the larger mesh continues to remain firmly appositioned against the aortic lumen wall during the endothelialization process when the adjacent tissue could possibly grow larger.

The mesh needs to be larger only in the radial dimension, and not in the axial dimension (i.e. along the length of the aorta). The mesh can be designed and built to be larger by 1% to 15%, preferably 5% to 10%, than the then existing implantation site anatomy size in the radial dimension.

In any of the embodiments described herein, the filament may be a wire having any cross-section such as round, square, rectangular, etc. and the size of the wire may be adjusted in order to various properties of the prosthesis such as its profile in the collapsed configuration, its stiffness and strength, and other properties. In preferred embodiments, a round nitinol wire is used having a diameter of 0.004 inches to 0.008 inches.

Additionally, any of the prostheses may carry a therapeutic agent such as an antithrombotic agent, antibiotic, etc. for localized and controlled elution at the treatment site. One of skill in the art will also appreciate that the prosthesis described herein preferably has a mesh with a polymer or fabric cover disposed thereover, but the prosthesis could be a mesh only to support the damaged or diseased tissue, or the prosthesis could be the polymer or fabric cover only. Thus, the fabrication methods and delivery methods described herein apply to either embodiment of prosthesis.

While preferred embodiments of the present invention have been shown and described herein, it will be obvious to those skilled in the art that such embodiments are provided by way of example only. Numerous variations, changes, and substitutions will now occur to those skilled in the art without departing from the invention. For example, the devices are described with respect to a prosthetic aortic valve, however one of skill in the art that the devices and methods may also be applied to any heart valve such as the mitral valve, the tricuspid valve or the pulmonary valve. Additionally, the techniques described herein may be applied to any other valve in the body. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A personalized prosthetic valve for implantation at native valve treatment site, said personalized prosthetic valve comprising:
    a self-expanding mesh having a collapsed configuration and an expanded configuration, the collapsed configuration adapted to be delivered to the native valve treatment site, and the expanded configuration adapted to expand the valve into engagement with the treatment site, wherein the mesh in the expanded configuration is personalized prior to implantation to match the treatment site, wherein the mesh has an outer surface prior to implantation that substantially matches the native valve treatment site shape and size in the expanded configuration, and wherein the self-expanding mesh forms a central lumen configured to allow blood or other body fluids to pass therethrough, and
    wherein the valve further comprises a plurality of valve leaflets coupled to the self-expanding mesh and having an open configuration and a closed configuration,
    wherein in the open configuration the blood or the other body fluids are free to pass through the valve, and
    wherein in the closed configuration the plurality of leaflets are closer toward one another than in the open configuration, and the blood or the other body fluids are prevented from flowing upstream through the prosthetic valve.

2. The personalized prosthetic valve of claim 1, wherein the self-expanding mesh comprises a nitinol mesh.

3. The personalized prosthetic valve of claim 1, wherein the self-expanding mesh comprises one or more filaments in a helical pattern.

4. The personalized prosthetic valve of claim 1, wherein the self-expanding mesh comprises one or more filaments woven together to form overlapping regions with the one or more filaments overlapping one another at least once.

5. The personalized prosthetic valve of claim 1, wherein the self-expanding mesh comprises one or more filaments woven together to form a first overlapping region and a second overlapping region along a row, wherein in the first overlapping region the filaments overlap with one another a first number of times, and wherein in the second overlapping region the filaments overlap with one another a second number of times different than the first number of times.

6. The personalized prosthetic valve of claim 1, wherein the self-expanding mesh comprises barbs or hooks adapted to engage tissue at the treatment site and anchor the personalized prosthesis.

7. The personalized prosthetic valve of claim 1, wherein the self-expanding mesh comprises a plurality of overlapping filaments forming overlapping regions, and wherein the overlapping regions form raised surfaces adapted to engage tissue at the native valve treatment site and anchor the personalized prosthetic valve.

8. The personalized prosthetic valve of claim 1, further comprising a membrane disposed over the mesh, wherein the membrane is elastic and conforms to the self-expanding mesh, and wherein the membrane has an outer surface that substantially matches the native valve treatment site shape in the expanded configuration, and wherein the membrane forms the central lumen.

9. The personalized prosthetic valve of claim 8, wherein the membrane comprises a resilient polymer.

10. The personalized prosthetic valve of claim 1, further comprising one or more radiopaque markers coupled to the membrane or the self-expanding mesh for facilitating implantation of the personalized prosthetic valve at the native valve treatment site.

11. The personalized prosthetic valve of claim 1, further comprising one or more apertures extending through a sidewall of the personalized prosthetic valve, the one or more apertures fluidly coupled with the central lumen to allow blood flow or other fluids to flow between the central lumen and the one or more apertures, the one or more apertures configured to accommodate side branch vessels or other body passages such that the personalized prosthetic valve does not obstruct blood flow or fluid flow therethrough.

12. The personalized prosthetic valve of claim 11, wherein the one or more apertures are personalized prior to implantation of the personalized prosthetic valve to align with an anatomical location of one or more coronary ostia to permit the blood flow between the one or more apertures and the one or more coronary ostia without obstructing the one or more coronary ostia with the personalized prosthetic valve.

13. The personalized prosthetic valve of claim 1, wherein the native valve treatment site has a shape, and wherein the lumen has a shape substantially matching the shape of the native valve treatment site.

14. The personalized prosthetic valve of claim 1, wherein the lumen does not substantially alter blood flow path across the treatment site.

* * * * *

UNITED STATES PATENT AND TRADEMARK OFFICE
CERTIFICATE OF CORRECTION

| | | |
|---|---|---|
| PATENT NO. | : 10,292,815 B2 | Page 1 of 1 |
| APPLICATION NO. | : 15/638277 | |
| DATED | : May 21, 2019 | |
| INVENTOR(S) | : Hira V. Thapliyal | |

It is certified that error appears in the above-identified patent and that said Letters Patent is hereby corrected as shown below:

On the Title Page

In Column 2, under "Other Publications", Line 1, delete "(inlcuded" and insert --(included-- therefor On page 2, in Column 2, under "Other Publications", Line 7, delete "allowancedatedJun." and insert --allowance dated Jun.-- therefor On page 2, in Column 2, under "Other Publications", Line 24, delete "Sununary" and insert --Summary-- therefor In the Specification In Column 9, Line 40, delete "322" and insert --322.-- therefor In the Claims In Column 14, Line 42, in Claim 1, after "at", insert --a--

Signed and Sealed this
Seventeenth Day of March, 2020

Andrei Iancu
*Director of the United States Patent and Trademark Office*